(12) United States Patent
Khilevich et al.

(10) Patent No.: US 7,754,742 B2
(45) Date of Patent: Jul. 13, 2010

(54) IMIDAZOLE CARBOXAMIDES

(75) Inventors: Albert Khilevich, Westfield, IN (US); Bin Liu, Fishers, IN (US); Daniel Ray Mayhugh, Carmel, IN (US); Jeffrey Michael Schkeryantz, Fishers, IN (US); Deyi Zhang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/502,252

(22) Filed: Jul. 14, 2009

(65) Prior Publication Data

US 2010/0016373 A1 Jan. 21, 2010

Related U.S. Application Data

(60) Provisional application No. 61/081,774, filed on Jul. 18, 2008.

(51) Int. Cl.
*A61K 31/4172* (2006.01)
*A61K 31/4439* (2006.01)
*C07D 233/64* (2006.01)
*C07D 401/12* (2006.01)

(52) U.S. Cl. ............... 514/340; 514/399; 546/272.7; 548/333.5

(58) Field of Classification Search ............ 548/333.5; 546/272.7; 514/340, 399
See application file for complete search history.

(56) References Cited

FOREIGN PATENT DOCUMENTS

| EP | 0028063 B1 | 6/1984 |
|---|---|---|
| EP | 0174770 A1 | 6/1985 |
| EP | 0516069 A1 | 5/1992 |
| WO | WO 01/56990 A2 | 8/2001 |
| WO | 2004-018386 * | 3/2004 |
| WO | WO 2004/018386 A2 | 3/2004 |
| WO | WO 2006/014918 A2 | 2/2006 |
| WO | WO 2006/015158 A1 | 2/2006 |
| WO | WO 2006/020879 A1 | 2/2006 |
| WO | WO 2006/047237 A2 | 5/2006 |
| WO | 2006057860 A | 6/2006 |
| WO | WO 2006/057869 A1 | 6/2006 |
| WO | WO 2006/071730 A1 | 7/2006 |
| WO | WO 2007/021308 A1 | 2/2007 |
| WO | WO 2007/021309 A1 | 2/2007 |

* cited by examiner

*Primary Examiner*—Joseph K. McKane
*Assistant Examiner*—Janet L Coppins
(74) *Attorney, Agent, or Firm*—Mark A. Winter

(57) ABSTRACT

The present invention provides certain imidazole carboxamide derivatives, pharmaceutical compositions thereof, methods of using the same and processes for preparing the same.

16 Claims, No Drawings

IMIDAZOLE CARBOXAMIDES

This application claims the benefit of U.S. Provisional Application No. 61/081,774 filed Jul. 18, 2008.

The present invention provides certain imidazole carboxamide derivatives, pharmaceutical compositions thereof, methods of using the same, and processes for preparing the same.

L-Glutamate is the major excitatory neurotransmitter in the central nervous system and is referred to as an excitatory amino acid. Glutamate receptors are composed of two major subtypes: the ligand-gated ion-channel ionotropic receptors, and the G-protein-coupled seven-transmembrane-domain metabotropic receptors (mGluRs). The metabotropic family comprises eight members and is sub-divided into three groups based on sequence similarity, signal transduction, and pharmacology. Group I receptors (mGluR$_1$ and mGluR$_5$, and their splice variants) are positively coupled to inositol phosphate hydrolysis and the generation of an intracellular calcium signal. Group II receptors (mGluR$_2$ and mGluR$_3$) and Group III receptors (mGluR$_4$, mGluR$_6$, mGluR$_7$, and mGluR$_8$) are negatively coupled to adenylyl cyclase and regulate cyclic AMP levels by indirectly inhibiting adenylyl cyclase activity. The mGlu receptor subtypes have unique expression patterns in the central nervous system, which can be targeted with new and selective agents.

International Patent Application Publication No. WO 2004/057869 A1 discloses certain acetophenone derivative compounds as potentiators of mGluR2 receptors and antagonists of CysLT1 receptors, and further discloses the compounds as useful in the treatment of a number of conditions including depression, anxiety and migraine.

European Patent Application No. EP 0516069 discloses certain acetophenone derivative compounds as antagonists of leukotriene B4, and further discloses the compounds as useful in treating allergy, rheumatoid arthritis and inflammatory bowel disease.

The compounds of the present invention are selective potentiators of the Group II metabotropic receptors, particularly the mGluR$_2$ receptor (mGluR$_2$), especially with respect to mGluR$_1$, mGluR$_3$, mGluR$_4$, mGluR$_5$ and mGluR$_8$. As such they are believed to be useful for the treatment of conditions associated with the mGluR$_2$ receptor, such as depression including major depressive disorder, anxiety including generalized anxiety disorder, as well as depression co-morbid with anxiety (mixed depression anxiety disorder) including major depressive disorder co-morbid with generalized anxiety disorder.

Thus, the present invention provides new compounds that are potentiators of mGluR$_2$ and, as such, are believed to be useful in treatment of the disorders discussed above. Such new compounds could address the need for safe and effective treatments of conditions associated with the above receptors without attending side effects.

The present invention provides a compound of formula I, or a pharmaceutically acceptable salt thereof,

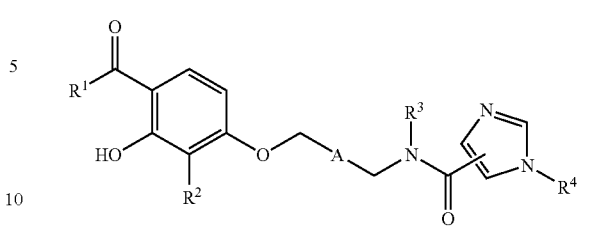

wherein
R$^1$ is C$_1$-C$_5$ alkyl, C$_3$-C$_5$ cycloalkyl, or C$_3$-C$_5$ cycloalkylmethyl;
R$^2$ is C$_1$-C$_3$ alkyl, chloro, bromo, fluoro or trifluoromethyl;
A is selected from the group consisting of

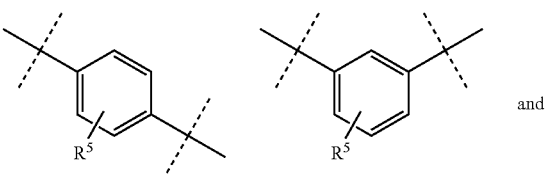

and

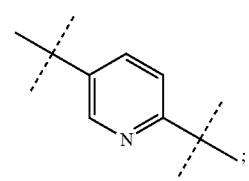

R$^3$ is hydrogen or methyl;
R$^4$ is hydrogen or C$_1$-C$_3$ alkyl; and
R$^5$ is one substituent selected from the group consisting of hydrogen, methyl, methoxy, chloro and fluoro; or two substituents which are fluoro.

Further, the present invention provides a pharmaceutical composition comprising a compound of the present invention, or a pharmaceutically acceptable salt thereof, and a pharmaceutically acceptable carrier, diluent or excipient.

Further, the present invention provides a compound of the present invention or a pharmaceutically acceptable salt thereof, for use in therapy.

Further, the present invention provides a compound of the present invention, or a pharmaceutically acceptable salt thereof, for use in the treatment of depression.

Further, the present invention provides the use of a compound of the present invention, or a pharmaceutically acceptable salt thereof, for the manufacture of a medicament for treating depression.

Further, the present invention provides a method of treating depression, comprising administering to a patient in need thereof an effective amount of a compound of formula I, or a pharmaceutically acceptable salt thereof.

A particular compound of formula I is the compound wherein -A- is

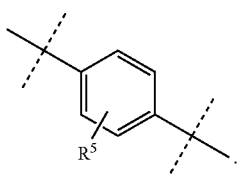

A particular compound of formula I is the compound of formula Ia or a pharmaceutically acceptable salt thereof

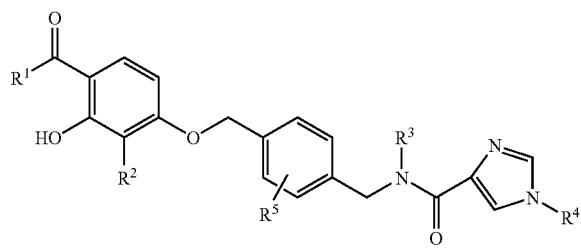

wherein $R^1$ is $C_1$-$C_5$ alkyl, $C_3$-$C_5$ cycloalkyl, or $C_3$-$C_5$ cycloalkylmethyl;

$R^2$ is $C_1$-$C_3$ alkyl, bromo, or trifluoromethyl;

$R^3$ is hydrogen or methyl;

$R^4$ is hydrogen or $C_1$-$C_3$ alkyl; and $R^5$ is one substituent selected from the group consisting of hydrogen, methyl, methoxy, chloro and fluoro; or two substituents which are fluoro.

A particular compound of formula I or Ia is one wherein $R^1$ is $C_1$-$C_5$ alkyl.

A particular compound of formula I or Ia is one wherein $R^2$ is trifluoromethyl.

A particular compound of formula I or Ia is one wherein $R^3$ is hydrogen.

A particular compound of formula I or Ia is one wherein $R^4$ is $C_1$-$C_3$ alkyl.

A particular compound of formula I or Ia is one wherein $R^5$ is hydrogen, methyl or methoxy.

A particular compound of formula I or Ia is one wherein $R^1$ is $C_1$-$C_5$ alkyl;

$R^2$ is trifluoromethyl;

$R^3$ is hydrogen;

$R^4$ is $C_1$-$C_3$ alkyl; and $R^5$ is hydrogen, methyl or methoxy.

A more particular compound of formula I or Ia is one wherein wherein $R^5$ is hydrogen.

A more particular compound of formula I or Ia is one wherein wherein $R^4$ is methyl.

A more particular compound of formula I or Ia is one wherein wherein $R^1$ is isopropyl.

A more particular compound of formula I or Ia is one wherein $R^1$ is isopropyl;

$R^2$ is trifluoromethyl;

$R^3$ is hydrogen;

$R^4$ is methyl; and $R^5$ is hydrogen.

A more particular compound of formula I is one wherein $R^1$ is methyl, ethyl, propyl, isopropyl, isobutyl, 2,2-dimethylpropyl, cyclopropyl, cyclobutyl, cyclopentyl, cyclopropylmethyl, cyclobutylmethyl or cyclopentylmethyl;

$R^2$ is methyl, trifluoromethyl or bromo;

A is selected from the group consisting of

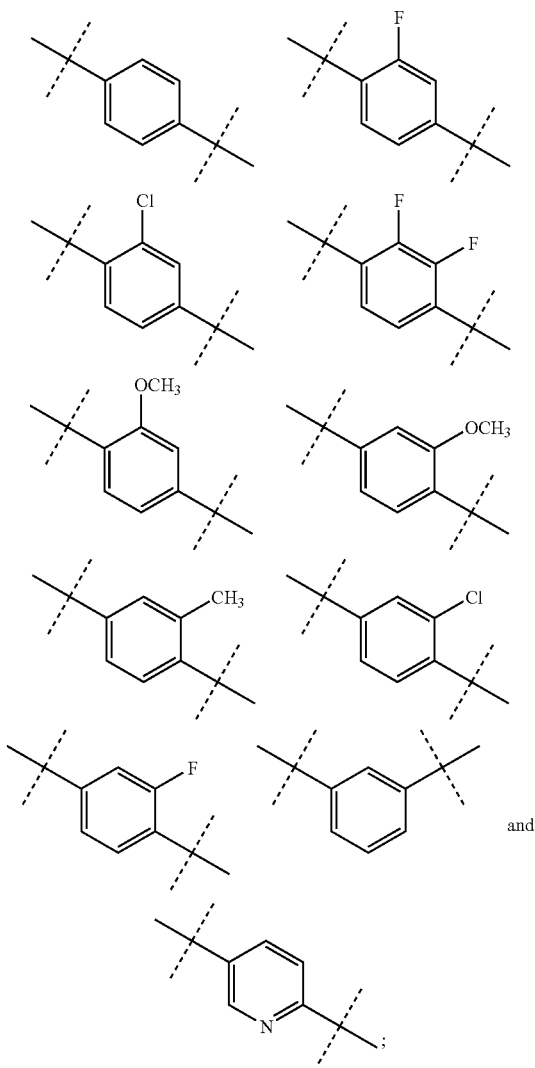

$R^3$ is hydrogen or methyl; and $R^4$ is hydrogen, methyl, ethyl or isopropyl.

A preferred compound of formula I or Ia is 1-methyl-1H-imidazole-4-carboxylic acid 4-(3-hydroxy-4-isobutyryl-2-trifluoromethyl-phenoxymethyl)-benzylamide or a pharmaceutically acceptable salt thereof.

A more preferred compound of formula I or Ia is 1-methyl-1H-imidazole-4-carboxylic acid 4-(3-hydroxy-4-isobutyryl-2-trifluoromethyl-phenoxymethyl)-benzylamide.

A further embodiment of the present invention include a process for preparing a compound of formula I, or a pharmaceutically acceptable salt thereof, comprising A) for a compound of formula I where $R^4$ is $C_1$-$C_3$ alkyl,

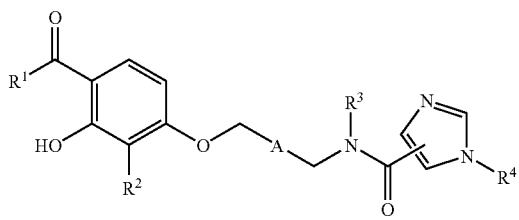

I coupling of a compound of formula II with an $R^4$-imidazole carboxylic acid where $R^4$ is $C_1$-$C_3$ alkyl

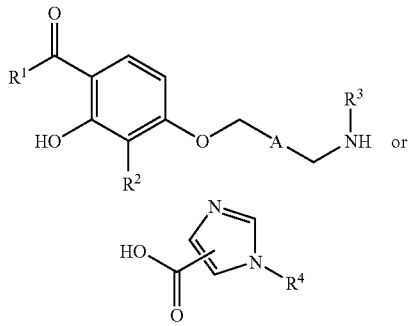

II

B) for a compound of formula I where $R^4$ is H, deprotecting a compound of formula VIII where Pg is an imidazole protecting group such as triphenylmethyl;

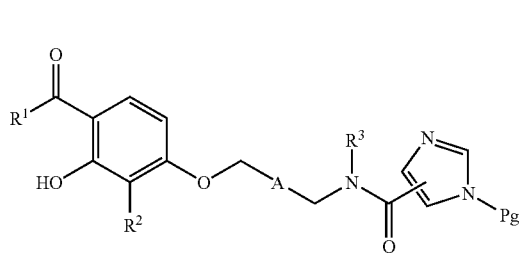

VIII whereafter, when a pharmaceutically acceptable salt of the compound of formula I is required, it is obtained by reacting a basic compound of formula I with a physiologically acceptable acid or by any other conventional procedure.

It is understood that compounds of the present invention may exist as stereoisomers. While all enantiomers, diastereomers, and mixtures thereof, are contemplated within the present invention, preferred embodiments are single diastereomers, and more preferred embodiments are single enantiomers.

It is understood that compounds of the present invention may exist as tautomeric forms. When tautomeric forms exist, each form and mixtures thereof, are contemplated in the present invention. For example, when the group $R^4$ is hydrogen, a compound of formula I may exist in tautomeric forms I and II. As such, it is understood any reference to a compound of formula I where the group $R^4$ is hydrogen as tautomeric form I encompasses tautomeric form II as well as mixtures of forms I and II.

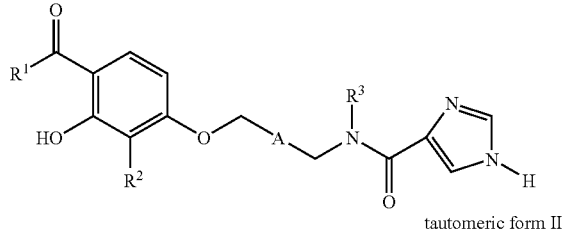

tautomeric form I

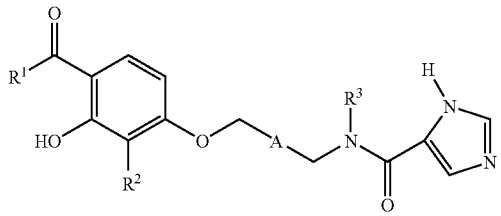

tautomeric form II

The term "pharmaceutically acceptable salt" includes acid addition salt that exists in conjunction with the basic portion of a compound of formula I. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan.

In addition to pharmaceutically acceptable salts, other salts are included in the invention. They may serve as intermediates in the purification of compounds or in the preparation of other pharmaceutically-acceptable salts, or are useful for identification, characterization or purification.

A compound of the invention is expected to be useful whenever potentiation of the mGluR$_2$ receptor is indicated. In particular, a compound of the invention is expected to be useful for the treatment of depression including major depressive disorder, anxiety including generalized anxiety disorder, as well as depression co-morbid with anxiety (mixed depression anxiety). Accordingly, one particular aspect of the invention is treatment of mixed depression anxiety disorder including major depressive disorder co-morbid with generalized anxiety disorder.

As used herein, the term "patient" refers to a warm blooded animal such as a mammal and includes a human.

It is also recognized that one skilled in the art may affect a depression disorder by treating a patient presently displaying symptoms with an effective amount of the compound of formula I. Thus, the terms "treatment" and "treating" are intended to refer to all processes wherein there may be a slowing, interrupting, arresting, controlling, or stopping of the progression of the disorder and/or symptoms thereof, but does not necessarily indicate a total elimination of all symptoms.

It is also recognized that one skilled in the art may affect a depression disorder by treating a patient at risk of future symptoms with an effective amount of the compound of formula I and is intended to include prophylactic treatment of such.

As used herein, the term "effective amount" of a compound of formula I refers to an amount, that is, the dosage which is effective in treating a depression disorder described herein.

The attending diagnostician can readily determine an effective amount by the use of conventional techniques and by observing results obtained under analogous circumstances. In determining an effective amount, the dose of a compound of formula I, a number of factors are considered by the attending diagnostician, including, but not limited to the compound of formula I to be administered; the co-administration of other agents, if used; the species of mammal; its size, age, and general health; the degree of involvement or the severity of depression; the response of the individual patient; the mode of administration; the bioavailability characteristics of the preparation administered; the dose regimen selected; the use of other concomitant medication; and other relevant circumstances.

An effective amount of a compound of formula I is expected to vary from about 0.01 milligram per kilogram of body weight per day (mg/kg/day) to about 5 mg/kg/day. Preferred amounts may be determined by one skilled in the art.

The compounds of the present invention can be administered alone or in the form of a pharmaceutical composition, that is, combined with pharmaceutically acceptable carriers or excipients, the proportion and nature of which are determined by the solubility and chemical properties, including stability, of the compound selected, the chosen route of administration, and standard pharmaceutical practice. The compounds of the present invention, while effective themselves, may be formulated and administered in the form of their pharmaceutically acceptable salts, for convenience of crystallization, increased solubility, and the like.

Thus, the present invention provides pharmaceutical compositions comprising a compound of the formula I and a pharmaceutically acceptable carrier, diluent or excipient.

One skilled in the art of preparing formulations can readily select the proper form and mode of administration depending upon the particular characteristics of the compound selected, the disorder or condition to be treated, the stage of the disorder or condition, and other relevant circumstances (REMINGTON: THE SCIENCE AND PRACTICE OF PHARMACY, 19th Edition, Mack Publishing Co. (1995)).

Functional in vitro activity at human mGluR$_2$ receptor Cell lines stably expressing the human mGluR$_2$ receptor (see for example Desai, Burnett, Mayne, Schoepp, Mol. Pharmacol. 48, 648-657, 1995) co-transfected with the rat glutamate transporter EAAT 1 (Excitatory Amino Acid Transporter 1) and the Gα15 subunit were used for these studies. The expression of Gα15 allows this Gi-coupled receptors to couple to phospholipase C, resulting in the ability to measure receptor activation by a fluorometric calcium response assay. The cell line was maintained by culturing in Dulbecco's Modified Eagle's Medium (DMEM) with high glucose and pyridoxine hydrochloride supplemented with 5% heat inactivated, dialyzed fetal bovine serum, 1 mM sodium pyruvate, 10 mM HEPES (4-(2-hydroxyethyl)-1-piperazineethanesulfonic acid), 1 mM of L-glutamine, and 5 μg/ml blasticidin. Confluent cultures were passaged biweekly using an enzyme-free dissociation solution. Cells were harvested 24 hours prior to assay and dispensed at 85K cells per well into 96-well, black-walled, poly-lysine-coated plates in medium containing only 250 μM L-glutamine (freshly added).

Intracellular calcium levels were monitored before and after the addition of compounds using a Fluorometric Imaging Plate Reader (FLIPR, Molecular Devices, Union City, Calif. USA). The assay buffer was comprised of Hank's Buffered Salt Solution (HBSS) supplemented with 20 mM HEPES. The medium was removed and the cells were incubated with 8 μM Fluo-3AM (Molecular Probes, Eugene, Oreg., USA, F-1241; 50 μL per well) in assay buffer for 90 minutes at 25° C. The dye solution was removed by tapping the plates and was replaced with fresh assay buffer (50 μL per well). A single-addition FLIPR assay generating an 11-point dose response curve for the agonist glutamate was conducted prior to each experiment. The results were analyzed (GraphPad® Prism v4, Graphpad Software, LaJolla, Calif., USA) to calculate the concentrations of glutamate needed to induce the EC10 responses.

Compounds were tested in a two-addition FLIPR assay using a 10-point concentration response profile starting at a final concentration of 25 μM (agonist mode) or 12.5 μM (potentiator mode). A three-fold dilution series in dimethyl sulfoxide (DMSO) was followed by a single dilution into assay buffer. After taking an initial fluorescent read of the cell plate for 5 seconds, compound was added to the cell plate (50 uL per well). Data were collected every second for the first 30 seconds and then every 3 seconds in order to detect agonist activity until the second addition was made after approximately 90 seconds. The second addition consisted of 100 μL of glutamate in assay buffer (typically about 1 μM) generating a response measuring 10% of controls ($EC_{10}$). Following the second addition, data were collected every 3 seconds for approximately 90 seconds.

The maximal response was defined as that induced by ECmax (100 μM glutamate). The compound effect was measured as maximal minus minimal peak heights in relative fluorescent units (RFUs) corrected for basal fluorescence measured in the absence of glutamate. Determinations were carried out using single plates. Agonist effects were quantified as percent stimulation induced by compound alone relative to the maximal glutamate response. Potentiation effects were quantified as percent increase in agonist $EC_{10}$ response relative to the ECmax response. All data were calculated as relative $EC_{50}$ values using a four-parameter logistic curve fitting program (ActivityBase® v5.3.1.22, IBS, Alamenda, Calif., USA).

In the above assay, compounds exemplified herein exhibit an $EC_{50}$ of less than 150 nM at mGluR$_2$. For example, the compound of Example 1 exhibits an $EC_{50}$ of 22.5 nM measured at mGluR$_2$. This demonstrates that compounds of the present invention are potent potentiators of the mGluR$_2$ receptor.

Positive Differential Reinforcement in Rats

The differential reinforcement of low rates-72 second (DRL-72) schedule has been extensively used as a screen for clinically effective antidepressant agents including imipramine, fluoxetine, paroxetine and others (Sokolowski J D, Seiden L S. 1999. The behavioral effects of sertraline, fluoxetine, and paroxetine differ on the differential-reinforcement-of-low-rate 72-second operant schedule in the rat. Psychopharm (Berl). 147(2): 153-61). The variety of positive results reported in this assay indicates that compounds with various mechanisms of action in human clinical studies, are also effective in this assay system. Besides serotonin reuptake inhibitors such as fluoxetine, compounds which inhibit the uptake of norepinephrine, such as imipramine or reboxetine, have also been found to produce positive effects in this assay. As such, compounds which show positive result in differential reinforcement in animals are believed to be useful in treating depression in humans.

Male Holtzman Sprague-Dawley rats are water restricted (water available 20' per day following the test session) and trained to lever press for a 4" access to 0.025 ml of water for each correct response during daily 60 minute sessions. All testing takes place on weekdays only. After successful lever press training, rats are then required to respond under a DRL-24 second schedule, where only lever presses that are separated by 24 seconds are reinforced. Upon stable responding on a DRL-24 second schedule, rats are trained on a DRL-72 second schedule until responding stabilizes at approximately 15% efficiency. Specifically, rats receive a reinforcer for each response that is emitted at least 72 seconds after the previous response (IRT). Responses with IRT's less than 72 seconds do not receive a reinforcer, and the IRT requirement is reset to 72 seconds. Response efficiency is recorded as number of reinforced responses divided by total number of responses. After stable baseline responding is achieved, defined as responding for 3 consecutive sessions with no more than 10% variability, animals begin drug testing. Animals receive drug no more than 1 time per week. Data collected includes number of responses emitted, number of reinforcers received and the IRT. Positive drug effects include a reduction in overall responding, an increase in reinforcers received, and an orderly shift to the right of the IRT distribution curve, indicating animals are approximating the 72 second interval more efficiently without loss of stimulus control of the schedule.

TABLE A

| Example Number | Dose (mg/kg, IP) | Reinforcers Received, mean (±SEM) | Responses Emitted, mean (±SEM) | Response Efficiency |
|---|---|---|---|---|
|  | 0 | 15.2 (1.6) | 70 (4.9) | 0.25 |
| 1 | 10 | 21 (2.6) | 45.2 (6.4) | 0.56 |

In the above assay, the compound of Example 1 exhibits an increase in reinforcements received and a significant reduction responses emitted at a dose of 10 mg/kg (Table A). This demonstrates that a compound of the present invention is useful in an in vivo model of depression.

Attenuation of Stress-Induced Hyperthermia in Rats

Hyperthermia, a rise in core body temperature, is a general phenomenon that has been reliably demonstrated in many mammals, including humans, in response to stress. In many anxiety disorders, hyperthermia occurs as part of the pathology and is considered a symptom of the disease. Compounds which attenuate stress-induced hyperthermia in animals are believed to be useful in treating anxiety disorders in humans.

The conventional and minimally-invasive method for analyzing stress-induced hyperthermia is by measuring body temperature, and stress-induced increases in body temperature, via rectal thermometer. Male Fischer F-344 rats (Harlan, Indianapolis, Ind., USA) weighing between 275-350 g are tested. All animals are individually-housed with food and automated water available ad libitum, and maintained on a 12 h light/dark cycle (lights on at 06:00). Animals are fasted for approximately 12-18 hours before the experiment, which is conducted during the light phase. Rats are dosed p.o. in a dose volume of 2 mL/kg with test compounds in the range of 1, 3, 10, and 30 mg/kg (suspended in 1% carboxymethylcellulose, 0.25% polysorbate 80, 0.05% antifoam). The mGluR$_5$ antagonist MTEP (3-[(2-methyl-1,3-thiazol-4-yl)ethynyl]pyridine), which has demonstrated robust anxiolytic-like activity in preclinical models, is used as a comparator (10 mg/kg, p.o., dissolved in water). Immediately following dosing, rats are returned to their home cage, and the experimenter turns off the lights and leaves the room. The dosing room is darkened for the remainder of the 4 hr pretreatment period.

After the pretreatment period, rats are taken individually to a brightly lit adjacent room where baseline body temperatures are determined by insertion of a rectal probe lubricated with mineral oil. Body temperature is assessed using a PHYS-ITEMP BAT-12® Microprobe Thermometer with a PHYS-ITEMP RET-2® rat rectal probe (Physitemp Instruments Inc., Clifton, N.J., USA). The probe is inserted approximately 2 cm into the rectum, to measure the core body temperature (this is the baseline body temperature, T1, in degrees Celsius). Ten minutes later a second body temperature measurement is recorded (T2). The difference in body temperature (T2-T1) is defined as the stress-induced hyperthermic response. The dose at which a compound produces a 35% reduction in stress-induced hyperthermic response, relative to the vehicle response, is defined as the T35 dose.

In the above assay, the compound of Example 1 produces a reduction in stress-induced hyperthermia with a T35 dose=3.2 mg/kg. This demonstrates that a compound of the present invention is useful in an in vivo model of anxiety.

A compound of formula I may be prepared by processes which include processes known in the chemical art for the production of structurally analogous compounds or by a process described herein including the processes described for the Preparations and Examples. A novel process described herein provides another aspect of the invention. A process for the preparation of a compound of formula I, or a pharmaceutically acceptable salt thereof, and novel intermediates for the manufacture of a compound of formula I provide further features of the invention and are illustrated by the following procedures in which the meaning of the generic radicals are as defined above, unless otherwise specified.

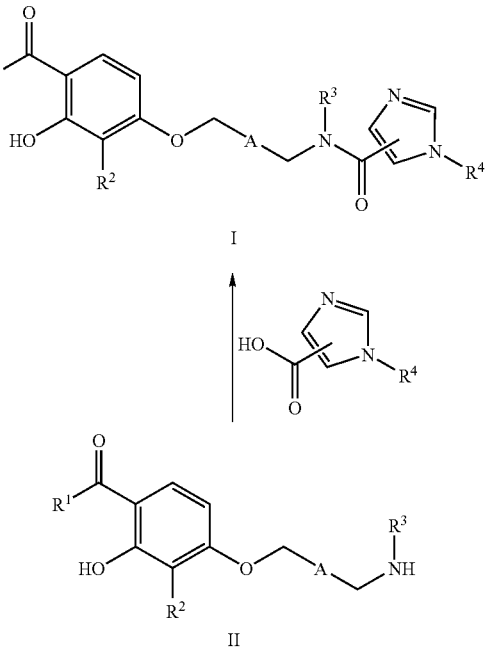

Scheme A

Generally, a compound of formula I may be prepared from a compound of formula II. More specifically in Scheme A, an amine of formula II is coupled with an imidazole carboxylic acid, 1-hydroxybenzotriazole and a carbodiimide reagent in a suitable solvent such as tetrahydrofuran to provide an amide of formula I where $R^4$ is $C_1$-$C_3$ alkyl. Suitable carbodiimide reagents include 1-(3-dimethylaminopropyl)-3-ethylcarbodiimide hydrochloride. For an amide of formula I where $R^4$ is hydrogen, the coupling is performed with an imidazole carboxylic acid where the $R^4$ hydrogen is replaced with a suitable protecting group such as triphenylmethyl. Removal of the protecting group provides an amide of formula I where $R^4$ is hydrogen.

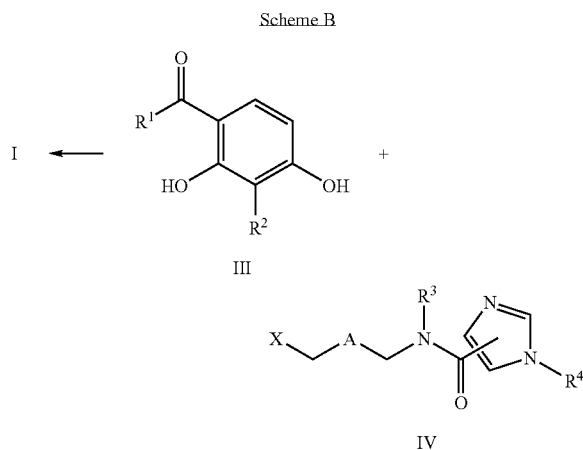

Scheme B

A compound of formula I may also be prepared from a compound of formula III. More specifically in Scheme B, a phenol of formula III is reacted under Mitsunobu conditions with a compound of formula IV where X is OH in the presence of an organophosphine such as triphenylphosphine and an appropriate azodicarbonyl reagent such as diisopropyl azodicarboxylate to provide a compound of formula I. Suitable solvents include toluene. Alternatively, a compound of formula I may be prepared by reacting a compound of formula III with a compound of formula IV where X is a leaving group in the presence of a base such as lithium carbonate and a suitable solvent such as DMF. Suitable leaving groups include halides such as iodide or bromide, and sulfonate esters such as methanesulfonate ester.

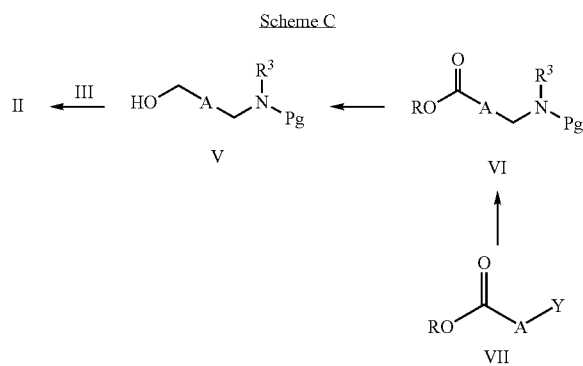

Scheme C

A compound of formula II may be prepared from a compound of formula VII. More specifically in Scheme C, a compound of formula VII where Y is cyano or azidomethyl is reacted with a suitable reducing agent to provide a compound of formula VII where y is aminomethyl. Protection of the aminomethyl group provides a compound of formula VI which is subsequently reacted with a reducing agent such as lithium aluminum hydride in a solvent such as tetrahydrofuran to provide a hydroxyl compound of formula V. Further, a hydroxyl compound of formula V may be directly reacted with a compound of formula III or converted to a suitable leaving group prior to reaction with compound III to provide a compound of formula II as described in Scheme B.

In the following illustrative preparations and examples, the following meanings and abbreviations are used throughout: DMSO, dimethyl sulfoxide (perdeuterated [-$d_6$] if for NMR); MS, mass spectrum; EtOAc, ethyl acetate; THF, tetrahydrofuran; min, minutes; HPLC, high pressure liquid chromatography; LC-MS, HPLC-mass spectrography; GC, gas chromatography; MeOH, methanol; MTBE, methyl t-butyl ether; SCX-2, cation exchange resin; mp, melting point; and NMR, nuclear magnetic resonance spectroscopy or spectrum. Reagents were obtained from a variety of commercial sources. Solvents are generally removed under reduced pressure (evaporated). In some preparations indicated yields are representative crude yields for products which are isolated by evaporation or filtration and used directly without further purification. HPLC is performed on a Waters 600 using Empower version 2 software; column: Chromolith Performance RP-18e, 4.6×100 mm; flow rate: 5 mL/min; gradient: 10% solvent A (0.1% trifluoroacetic acid in acetonitrile), 90% solvent B (0.1% trifluoroacetic acid in water) for 1 min, increased linearly to 80% solvent A over 4 min, hold at 80% solvent A for 3 min; detector: Waters PDA 996 using PDA single 254 channel.

Preparation 1

1-(2,4-Dihydroxy-phenyl)-2-methyl-propan-1-one

Combine resorcinol (1010 g, 9.17 mol) in boron trifluoride etherate (1.9 L, 15.0 mol) and mechanically stir in a 12-L Morton flask at room temperature. Treat mixture with isobutyryl chloride (880 mL, 8.37 mol), neat, over a 3 hour period via addition funnel, then stir overnight at room temperature. Pour the cooled oil into ~10 kg of cracked ice and extract twice with ethyl ether (5 L total). Wash organic layers with water, saturated sodium chloride solution, dry with magnesium sulfate, filter, and evaporate filtrate to provide the title compound (1636 g, quantitative yield) as a reddish oil. HPLC $R_t$=4.29 min; $^1$H NMR (CDCl$_3$) δ 13.03 (s, 1H), 7.69 (d, J=12.0 Hz, 1H), 6.4 (m, 2H), 3.51 (hept, J=8.0 Hz, 1H), 1.23 (d, J=8.0 Hz, 6H).

The following compound is prepared essentially by the method of Preparation 1.

| Prep. No. | Chemical name | Physical data |
|---|---|---|
| 2 | 1-(2,4-Dihydroxy-phenyl)-3,3-dimethyl-butan-1-one | $^1$H NMR (DMSO-d$_6$) δ 12.9 (bs, 1H), 7.80 (d, J = 8.0 Hz, 1H), 6.33 (dd, J = 2.8, 8.0 Hz, 1H), 6.31 (d, J = 2.8 Hz, 1H), 2.76 (s, 2H), 0.98 (s, 9H) |

Preparation 3

1-(2,4-Dihydroxy-phenyl)-3-methyl-butan-1-one

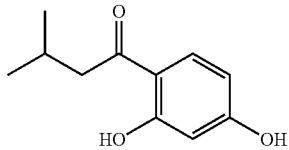

Add isovaleric acid (5.10 g, 50 mmol, 5.5 mL) in one portion to a mixture of resorcinol (5.00 g, 45.4 mmol) in boron trifluoride etherate (38.67 g, 272.5 mmol, 34.5 mL) at room temperature under Argon gas. Heat the reaction mixture at 90° C. for 1.5 hr. Cool the reaction to room temperature and pour it into a 20% aqueous sodium acetate solution and stir overnight. Extract the aqueous mixture with ethyl acetate (3×). Combine the organic layers, wash with saturated aqueous sodium bicarbonate solution and brine sequentially. Dry the organic phase over sodium sulfate, filter and concentrate under reduced pressure to provide the product as a brownish oil (9.80 g; 50.5 mmol, 111% yield). MS (m/z): 195 (M+1).

The following compounds are prepared essentially by the method of Preparation 3.

| Prep. No. | Chemical name | Physical data |
|---|---|---|
| 4 | 1-(2,4-Dihydroxy-phenyl)-butan-1-one | MS (m/z): 181 (M + 1) |
| 5 | 1-(2,4-Dihydroxy-phenyl)-2-methyl-propan-1-one | MS (m/z): 181 (M + 1) |
| 6 | Cyclopropyl-(2,4-dihydroxy-phenyl)-methanone | MS (m/z): 179 (M + 1) |
| 7 | Cyclobutyl-(2,4-dihydroxy-phenyl)-methanone | MS (m/z): 193 (M + 1) |
| 8 | 2-Cyclobutyl-1-(2,4-dihydroxy-phenyl)-ethanone | MS (m/z): 207 (M + 1) |
| 9 | Cyclopentyl-(2,4-dihydroxy-phenyl)-methanone | MS (m/z): 207 (M + 1) |
| 10 | 2-Cyclopentyl-1-(2,4-dihydroxy-phenyl)-ethanone | MS (m/z): 221 (M + 1) |

Preparation 11

1-Bromo-2,4-bis-(tert-butyl-dimethyl-silanyloxy)-benzene

Stir 4-bromoresorcinol (50 g, 265 mmol) in toluene (1 L) and treat with tert-butyldimethylchlorosilane (90 g, 597 mmol) and 1H-imidazole (50 g, 734 mmol). Heat to reflux for 6 hrs, then stir overnight at room temperature. Wash organic layer with water, dilute sodium hydroxide solution and brine, dry with magnesium sulfate, filter, and evaporate to provide the title compound as an amber oil (88.3 g, 80% yield). $^1$H NMR (CDCl$_3$) δ 7.31 (d, J=8.0 Hz, 1H), 6.37 (m, 2H), 1.04 (s, 6H), 0.97 (s, 6H), 0.24 (s, 3H), 0.19 (s, 3H).

Preparation 12

2-Cyclopropyl-N-methoxy-N-methyl-acetamide

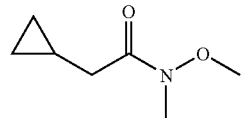

Stir cyclopropaneacetic acid (30 g, 300 mmol) in dichloromethane (1 L) and treat with 1,1'-carbonyldiimidazole (52.5 g, 324 mmol) slowly. Stir for 2 hrs at room temperature and treat with N,O-dimethylhydroxylamine hydrochloride (30 g, 308 mmol), neat, in one portion; stir overnight. Pour mixture into water and extract twice with dichloromethane. Wash organic layers with water, dilute hydrochloric acid, saturated sodium bicarbonate solution, dry with magnesium sulfate, filter, and evaporate to provide the title compound (38 g, 89%). $^1$H NMR (CDCl$_3$) δ 3.66 (s, 3H), 3.18 (s, 3H), 2.35 (d, J=8.0 Hz, 2H), 1.08 (m, 1H), 0.54 (m, 2H), 0.16 (m, 2H).

Preparation 13

2-Cyclopropyl-1-(2,4-dihydroxy-phenyl)-ethanone

Stir 1-bromo-2,4-bis-(tert-butyl-dimethyl-silanyloxy)-benzene (100 g, 240 mmol) in diethyl ether (1 L, anhydrous) at −60° C. and treat with 1.7M tert-butyllithium in pentane (290 mL, 493 mmol) via addition funnel over a 10 minute period. Stir for 15 min, then treat with 2-cyclopropyl-N-methoxy-N-methyl-acetamide (34 g, 237 mmol) in a minimum amount of ethyl ether. Remove cold bath, stir for 1 hr, treat with 1N aqueous hydrochloric acid (100 mL), and stir for an additional hour. Separate the layers and wash the organic layer with 1N aqueous hydrochloric acid (100 mL), brine, dry with magnesium sulfate, filter, and evaporate. Dissolve the residue in tetrahydrofuran (1 L), treat with 1N tetrabutylammonium fluoride solution in tetrahydrofuran (500 mL, 500 mmol), and stir for 3 hrs. Pour mixture into 1 L of water containing 120 mL of 5N hydrochloric acid, separate layers, and extract water layer twice with ethyl acetate. Wash organic layers with brine, dry with magnesium sulfate, filter, and evaporate. Chromatograph residue on silica gel (Biotage® Radial Compression fitted with a 75-L column) eluting with 25% ethyl acetate in hexanes to isolate the title compound (43 g, 94% yield). $^1$H NMR (CDCl$_3$) δ 12.83 (s, 1H), 7.60 (d, J=8.0 Hz, 1H), 6.39 (m, 2H), 5.98 (s, 1H), 2.80 (d, J=4.0 Hz, 2H), 1.13 (m, 1H), 0.60 (m, 2H), 0.22 (m, 2H).

Preparation 14

1-(2,4-Dihydroxy-3-iodo-phenyl)-2-methyl-propan-1-one

Mechanically stir suspensions of 1-(2,4-dihydroxy-phenyl)-2-methyl-propan-1-one (818 g, 4.54 mol) in ethanol (3 L) and water (6 L) in two separate 22-L Morton flasks. Treat each suspension with potassium iodate (170 g, 794 mmol) and iodine (410 g, 1.62 mol) and allow to stir over night at room temperature. Dilute the mixtures with water (2 L), adjust pH to 4 by adding 5N hydrochloric acid, then extract twice with 4 L of ethyl acetate. Wash organic layers once with dilute aqueous sodium bisulfite, brine, dry with magnesium sulfate, filter, combine both filtrates, and evaporate to 2.6 Kg of a black solid. Chromatograph 500 g portions of the solid on 3.5 Kg of silica gel, eluting with 80% dichloromethane in heptane to provide the title compound (1357 g, 49% yield) in approximately 97% purity (HPLC shows 97% purity, with 3% 3,5-diiodo analog; LCMS confirms both. HPLC $R_t$=4.75 min; $^1$H NMR (CDCl$_3$) δ 14.07 (s, 1H), 7.72 (d, J=8.0 Hz, 1H), 6.62 (d, J=8.0 Hz, 1H), 6.02 (s, 1H), 3.53 (hept, J=8.0 Hz, 1H), 1.24 (d, J=8.0 Hz, 6H); MS (m/z): 307.0 (M+1).

Preparation 15

1-(2,4-Dihydroxy-3-iodo-phenyl)-3-methyl-butan-1-one

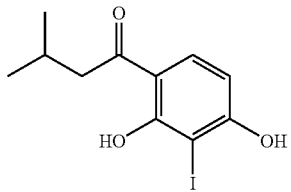

Add iodine (4.99 g, 19.7 mmol) and potassium iodate (2.16 g, 10.1 mmol) to a solution of 12,4-dihydroxy-phenyl)-3-methyl-butan-1-one (9.80 g, 50.5 mmol) in ethanol (50 mL) and water (80 mL) at room temperature. Stir the reaction vigorously overnight. Dilute the reaction with water, extract the mixture with ethyl acetate (3×). Combine the organic layers, wash with brine, dry over sodium sulfate, filter and concentrate under reduced pressure to provide the product as an oil (15.00 g, 46.9 mmol, 93% yield). MS (m/z): 321 (M+1).

The following compounds are prepared essentially by the method of Preparation 15.

| Prep. No. | Chemical name | Physical data |
|---|---|---|
| 16 | 1-(2,4-Dihydroxy-3-iodo-phenyl)-ethanone | $^1$H NMR (CDCl$_3$) δ 13.77 (s, 1H), 7.66 (d, J = 8.0 Hz, 1H), 6.62 (d, J = 8.0 Hz, 1H), 6.04 (s, 1H), 2.60 (s, 3H) |
| 17 | 1-(2,4-Dihydroxy-3-iodo-phenyl)-propan-1-one | $^1$H NMR (DMSO-d$_6$) δ 13.74 (s, 1H), 11.50 (s, 1H), 7.82 (d, J = 8.0 Hz, 1H), 6.52 (d, J = 8.0 Hz, 1H), 2.98 (q, J = 8.0 Hz, 2H), 1.07 (t, J = 8.0 Hz, 3H) |
| 18 | 1-(2,4-Dihydroxy-3-iodo-phenyl)-butan-1-one | MS (m/z): 305 (M − 1) |
| 19 | 1-(2,4-Dihydroxy-3-iodo-phenyl)-2-methyl-propan-1-one | MS (m/z): 305 (M − 1) |
| 20 | Cyclopropyl-(2,4-dihydroxy-3-iodo-phenyl)-methanone | MS (m/z): 305 (M + 1) |
| 21 | 2-Cyclopropyl-1-(2,4-dihydroxy-3-iodo-phenyl)-ethanone | $^1$H NMR (CDCl$_3$) δ 13.89 (s, 1H), 7.65 (d, J = 8.0 Hz, 1H), 6.61 (d, J = 8.0 Hz, 1H), 6.03 (s, 1H), 2.84 (d, J = 8.0 Hz, 2H), 1.14 (m, 1H), 0.61 (m, 2H), 0.22 (m, 2H) |
| 22 | Cyclobutyl-(2,4-dihydroxy-3-iodo-phenyl)-methanone | MS (m/z): 316 (M − 1) |
| 23 | 2-Cyclobutyl-1-(2,4-dihydroxy-3-iodo-phenyl)-ethanone | MS (m/z): 331 (M − 1) |
| 24 | Cyclopentyl-(2,4-dihydroxy-3-iodo-phenyl)-methanone | MS (m/z): 331 (M − 1) |
| 25 | 1-(2,4-Dihydroxy-3-iodo-phenyl)-3,3-dimethyl-butan-1-one | $^1$H NMR (DMSO-d$_6$) δ 14.12 (s, 1H), 11.54 (s, 1H), 7.90 (d, J = 8.0 Hz, 1H), 6.51 (d, J = 8 Hz, 1H), 2.82 (s, 2H), 0.98 (s, 9H) |
| 26 | 2-Cyclopentyl-1-(2,4-dihydroxy-3-iodo-phenyl)-ethanone | MS (m/z): 347 (M + 1) |

Preparation 27

1-(2,4-Bis-benzyloxy-3-iodo-phenyl)-2-methyl-propan-1-one

Combine 1-(2,4-dihydroxy-3-iodo-phenyl)-2-methyl-propan-1-one (1357 g, 4.43 mol), benzyl bromide (1345 mL, 11.28 mol), and cesium carbonate (2460 g, 7.55 mol) in dimethylformamide (12 L) in a 22-L Morton flask and stir at room temperature overnight. Filter the salts and concentrate the filtrate (8 L of dimethylformamide is evaporated off). Combine residue with the salts, dilute with water (10 L) and extract with 2:1 ethyl acetate/toluene (2×6 L). Wash extracts with water (3×4 L), brine, dry with magnesium sulfate, filter, and evaporate. Stir the resulting solid in 9 L of 10% ethyl acetate in hexane for 1 hr, filter, wash solid with hexanes and air dry to provide the title compound (1710 g, 79% yield) as an off-white solid. HPLC $R_t$=6.60 min; $^1$H NMR (DMSO-$d_6$) δ 7.61 (d, J=8.0 Hz, 1H), 7.4 (m, 10H), 6.99 (d, J=8.0 Hz, 1H), 5.27 (s, 2H), 4.84 (s, 2H), 3.43 (hept, J=8.0 Hz, 1H), 0.99 (d, J=8.0 Hz, 6H).

room temperature under Argon gas. Stir the reaction at room temperature overnight. Filter the mixture and concentrate the filtrate under reduced pressure to an oil. Partition the oil between ether and water. Separate the organic layer and extract the aqueous layer with ether (2×). Combine the organic layers, wash with brine, dry over sodium sulfate, filter and concentrate to provide a redish oil (22.5 g, 45 mmol, 96% yield). MS (m/z): 501 (M+1).

The following compounds are prepared essentially by the method of Preparation 28.

| Prep. No. | Chemical name | Physical data |
|---|---|---|
| 29 | 1-(2,4-Bis-benzyloxy-3-iodo-phenyl)-ethanone | $^1$H NMR (CDCl$_3$) δ 7.69 (d, J = 8.0 Hz, 1H), 7.4 (m, 10H), 6.73 (d, J = 8.0 Hz, 1H), 5.24 (s, 2H), 4.96 (s, 2H), 2.56 (s, 3H) |
| 30 | 1-(2,4-Bis-benzyloxy-3-iodo-phenyl)-propan-1-one | $^1$H NMR (CDCl$_6$) δ 7.5 (m, 11H), 6.73 (d, J = 8.0 Hz, 1H), 5.23 (s, 2H), 4.94 (s, 2H), 2.94 (q, J = 8.0 Hz, 2H), 1.10 (t, J = 8.0 Hz, 3H) |
| 31 | 1-(2,4-Bis-benzyloxy-3-iodo-phenyl)-butan-1-one | MS (m/z): 509 (M + 23) |
| 32 | 1-(2,4-Bis-benzyloxy-3-iodo-phenyl)-2-methyl-propan-1-one | MS (m/z): 487 (M + 1) |
| 33 | (2,4-Bis-benzyloxy-3-iodo-phenyl)-cyclopropyl-methanone | — |
| 34 | 1-(2,4-Bis-benzyloxy-3-iodo-phenyl)-2-cyclopropyl-ethanone | $^1$H NMR (CDCl$_3$) δ 7.5 (m, 11H), 6.73 (d, J = 8.0 Hz, 1H), 5.23 (s, 2H), 4.94 (s, 2H), 2.83 (d, J = 8.0 Hz, 2H), 1.03 (m, 1H), 0.47 (m, 2H), 0.03 (m, 2H) |
| 35 | (2,4-Bis-benzyloxy-3-iodo-phenyl)-cyclobutyl-methanone | — |
| 36 | 1-(2,4-Bis-benzyloxy-3-iodo-phenyl)-2-cyclobutyl-ethanone | — |
| 37 | (2,4-Bis-benzyloxy-3-iodo-phenyl)-cyclopentyl-methanone | MS (m/z): 513 (M + 1) |
| 38 | 1-(2,4-Bis-benzyloxy-3-iodo-phenyl)-3,3-dimethyl-butan-1-one | $^1$H NMR (CDCl$_3$) δ 7.5 (m, 11H), 6.72 (d, J = 8.0 Hz, 1H), 5.22 (s, 2H), 4.93 (s, 2H), 2.89 (s, 2H), 0.93 (s, 9H) |
| 39 | 1-(2,4-Bis-benzyloxy-3-iodo-phenyl)-2-cyclopentyl-ethanone | — |

Preparation 28

1-(2,4-Bis-benzyloxy-3-iodo-phenyl)-3-methyl-butan-1-one

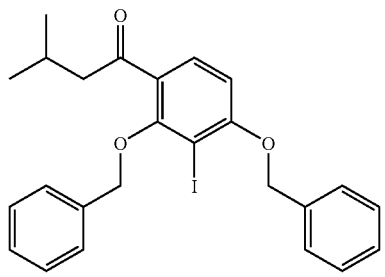

Add benzyl bromide (17.63 g, 103.1 mmol, 12.3 mL) and cesium carbonate (30.53 g, 93.7 mmol) to a solution of 1-(2,4-dihydroxy-3-iodo-phenyl)-3-methyl-butan-1-one (15.00 g, 46.9 mmol) in anhydrous dimethylformamide (120 mL) at Preparation 40

1-(2,4-Bis-benzyloxy-3-trifluoromethyl-phenyl)-2-methyl-propan-1-one

Stir 1-(2,4-bis-benzyloxy-3-iodo-phenyl)-2-methyl-propan-1-one (1500 g, 3.08 mol) in dimethylformamide (11 L) in a 22-L Morton flask and treat with methyl difluoro(fluorosulfonyl)acetate (1622 g, 8.44 mol), hexamethylphosphoric triamide (1475 mL, 8.47 mol), and copper(I) iodide (890 g, 4.67 mol). Degas via a glass fritted nitrogen inlet tube for 1 hr, then heat to 80° C. for 17 hrs and stir over the weekend at room temperature. Filter the solution away from the salts and concentrate the filtrate via reduced pressure (~10 L of solvent removed). Wash the salts with ethyl acetate (4 L), combine washings with the concentrated residue, and transfer the mixture to a 22 L separatory funnel. The mixture is further diluted with toluene (2 L), and washed with water (8 L) containing ammonium hydroxide (500 mL, conc) and ammonium chloride (250 g). Separate the layers and extract the water layer with 2:1 ethyl acetate/toluene (6 L). Combine the organic layers and wash with water (4 L) containing ammonium hydroxide (500 mL, conc) and ammonium chloride (250 g), water (4 L), saturated aqueous sodium chloride (4 L), dry with magnesium sulfate, filter, and evaporate the filtrate to provide the title compound (1460 g, 99% yield) as a reddish oil. HPLC $R_t$=6.51 min; $^1$H NMR (DMSO-$d_6$) δ 7.79 (d, J=8.0 Hz, 1H), 7.4 (m, 11H), 5.31 (s, 2H), 4.81 (s, 2H), 3.38 (hept, J=8.0 Hz, 1H), 1.00 (d, J=8.0 Hz, 6H); $^{19}$F NMR (DMSO-$d_6$) δ-54.40

Alternativily, the compound of Preparation 40 may be prepared by substituting hexamethylphosphoric triamide with dimethylformamide.

Preparation 41

1-(2,4-Bis-benzyloxy-3-trifluoromethyl-phenyl)-3-methyl-butan-1-one

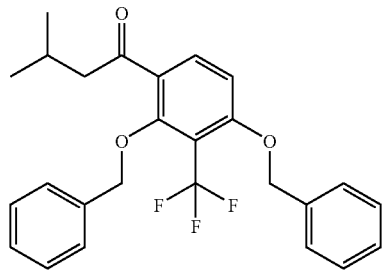

Add methyl difluoro(fluorosulfonyl)acetate (23.32 g, 121.4 mmol, 15.4 mL), copper(I) iodide (12.85 g, 67.5 mmol) to a solution of 1-(2,4-bis-benzyloxy-3-iodo-phenyl)-3-methyl-butan-1-one (22.5 g, 45 mmol) in dimethylacetamide (158 mL) and hexamethylphosphoric triamide (22 mL). Bubble argon through the reaction mixture for 5 min. Heat the reaction mixture at 80° C. overnight. Cool to room temperature, filter the solids and wash with ether. Transfer the filtrate to a separatory funnel and extract with ether (3×). Combine the organic layers, wash with water, saturated aqueous sodium bicarbonate solution and brine sequentially. Dry the organic phase over sodium sulfate, and concentrate to the title compound as a dark oil (19.1 g, 38.9 mmol, 86% yield). MS (m/z): 465 (M+23).

The following compounds are prepared essentially by the method of Preparation 41.

| Prep. No. | Chemical name | Physical data |
|---|---|---|
| 42 | 1-(2,4-Bis-benzyloxy-3-trifluoromethyl-phenyl)-ethanone | $^1$H NMR (CDCl$_3$) δ 7.72 (d, J = 8.0 Hz, 1H), 7.4 (m, 10H), 6.90 (d, J = 8.0 Hz, 1H), 5.24 (s, 2H), 4.90 (s, 2H), 2.52 (s, 3H) |
| 43 | 1-(2,4-Bis-benzyloxy-3-trifluoromethyl-phenyl)-propan-1-one | $^1$H NMR (CDCl$_3$) δ 7.67 (d, J = 8.0 Hz, 1H), 7.5 (m, 10H), 6.90 (d, J = 8.0 Hz, 1H), 5.22 (s, 2H), 4.88 (s, 2H), 2.90 (q, J = 8.0 Hz, 2H), 1.08 (t, J = 8.0 Hz, 3H) |
| 44 | 1-(2,4-Bis-benzyloxy-3-trifluoromethyl-phenyl)-butan-1-one | MS (m/z): 451 (M + 23) |
| 45 | 1-(2,4-Bis-benzyloxy-3-trifluoromethyl-phenyl)-2-methyl-propan-1-one | MS (m/z): 451 (M + 23) |
| 46 | (2,4-Bis-benzyloxy-3-trifluoromethyl-phenyl)-cyclopropyl-methanone | MS (m/z): 427 (M + 1) |
| 47 | 1-(2,4-Bis-benzyloxy-3-trifluoromethyl-phenyl)-2-cyclopropyl-ethanone | $^1$H NMR (CDCl$_3$) δ 7.69 (d, J = 8.0 Hz, 1H), 7.4 (m, 10H), 6.90 (d, J = 8.0 Hz, 1H), 5.23 (s, 2H), 4.88 (s, 2H), 2.79 (d, J = 4.0 Hz, 2H), 1.00 (m, 1H), 0.46 (m, 2H), 0.01 (m, 2H) |
| 48 | (2,4-Bis-benzyloxy-3-trifluoromethyl-phenyl)-cyclobutyl-methanone | — |
| 49 | 1-(2,4-Bis-benzyloxy-3-trifluoromethyl-phenyl)-2-cyclobutyl-ethanone | — |
| 50 | (2,4-Bis-benzyloxy-3-trifluoromethyl-phenyl)-cyclopentyl-methanone | MS (m/z): 477 (M + 23) |

-continued

| Prep. No. | Chemical name | Physical data |
|---|---|---|
| 51 | 1-(2,4-Bis-benzyloxy-3-trifluoromethyl-phenyl)-3,3-dimethyl-butan-1-one | $^1$H NMR (CDCl$_3$) δ 7.61 (d, J = 8.0 Hz, 1H), 7.5 (m, 10H), 6.90 (d, J = 8.0 Hz, 1H), 5.21 (s, 2H), 4.89 (s, 2H), 2.86 (s, 2H), 0.93 (s, 9H) |
| 52 | 1-(2,4-Bis-benzyloxy-3-trifluoromethyl-phenyl)-2-cyclopentyl-ethanone | — |

Preparation 53

1-(2,4-Dihydroxy-3-trifluoromethyl-phenyl)-2-methyl-propan-1-one

Stir 1-(2,4-bis-benzyloxy-3-trifluoromethyl-phenyl)-2-methyl-propan-1-one (1460 g, 3.07 mol) in dimethyl sulfide (8 L, 108.81 mol), treat with methanesulfonic acid (2.5 L, 38.13 mol), then gently reflux overnight. Cool mixture to 33° C. and treat with cracked ice (~6 Kg) at such a rate as to keep the mixture below reflux. Transfer mixture to a separatory funnel, separate layers, and extract water layer with ethyl acetate (6 L). Wash organic layers with water (4 L), saturated sodium chloride solution (4 L), dry with magnesium sulfate, filter, and evaporate to a solid. Re-crystallize the solid from toluene (4 L) to afford 527 g of 1-(2,4-dihydroxy-3-trifluoromethyl-phenyl)-2-methyl-propan-1-one as a tan solid (3 crops). The filtrate is concentrated to 380 g of a black gritty oil and filtered through a pad of silica gel to provide 216 g of a yellow solid, which is re-crystallized from toluene to afford 69 g of additional material. All lots are combined to provide the title compound (596 g, 78% yield): HPLC R$_t$=4.98 min; $^1$H NMR (DMSO-d$_6$) δ 14.15 (s, 1H), 11.70 (s, 1H), 8.06 (d, J=8.0 Hz, 1H), 6.57 (d, J=8.0 Hz, 1H), 3.62 (hept, J=8.0 Hz, 1H), 1.11 (d, J=8.0 Hz, 6H); $^{19}$F NMR (DMSO-d$_6$) δ-54.50; MS (m/z): 249.0 (M+1).

Preparation 54

1-(2,4-Dihydroxy-3-trifluoromethyl-phenyl)-3-methyl-butan-1-one

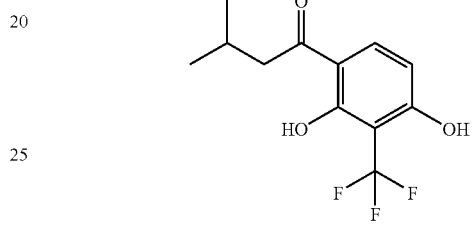

Add methanesulfonic acid (41 mL) to a solution of 1-(2,4-bis-benzyloxy-3-trifluoromethyl-phenyl)-3-methyl-butan-1-one (19.1 g, 38.9 mmol) in dimethyl sulfide (146 mL) at room temperature under argon gas. Heat the reaction mixture gently to reflux overnight. Quench the reaction mixture with ice-water and stir for 1 hr. Separate the organic layer and extract the aqueous with ethyl acetate (3×). Combine the organic layers, wash with brine, dry over sodium sulfate, and concentrate to give a crude oil. Purify the resulting crude oil by flash column chromatography (silica gel) eluting with 25% ethyl acetate/hexane to provide the title compound as a tan solid (5.3 g, 20.2 mmol, 52% yield). MS (m/z): 263 (M+1).

The following compounds are prepared essentially by the method of Preparation 54.

| Prep. No. | Chemical name | Physical data |
|---|---|---|
| 55 | 1-(2,4-Dihydroxy-3-trifluoromethyl-phenyl)-ethanone | $^1$H NMR (DMSO-d$_6$) δ 13.95 (s, 1H), 11.70 (s, 1H), 7.99 (d, J = 8.0 Hz, 1H), 6.55 (d, J = 8.0 Hz, 1H), 2.55 (s, 3H) |
| 56 | 1-(2,4-Dihydroxy-3-trifluoromethyl-phenyl)-propan-1-one | $^1$H NMR (CDCl$_3$) δ 13.90 (s, 1H), 7.80 (d, J = 8.0 Hz, 1H), 6.77 (q, J = 8.0 Hz, 1H), 6.49 (d, J = 8.0 Hz, 1H), 2.97 (q, J = 8.0 Hz, 2H), 1.23 (t, J = 8.0 Hz, 3H) |
| 57 | 1-(2,4-Dihydroxy-3-trifluoromethyl-phenyl)-butan-1-one | MS (m/z): 247 (M − 1) |
| 58 | 1-(2,4-Dihydroxy-3-trifluoromethyl-phenyl)-2-methyl-propan-1-one | MS (m/z): 247 (M − 1) |
| 59 | 2-Cyclopropyl-1-(2,4-dihydroxy-3-trifluoromethyl-phenyl)-ethanone | $^1$H NMR (DMSO-d$_6$) δ 14.05 (s, 1H), 11.68 (s, 1H), 7.99 (d, J = 8.0 Hz, 1H), 6.54 (d, J = 8.0 Hz, 1H), 2.89 (d, J = 4.0 Hz, 2H), 1.01 (m, 1H), 0.48 (m, 2H), 0.17 (m, 2H) |
| 60 | Cyclobutyl-(2,4-dihydroxy-3-trifluoromethyl-phenyl)-methanone | MS (m/z): 259 (M − 1) |

-continued

| Prep. No. | Chemical name | Physical data |
|---|---|---|
| 61 | 2-Cyclobutyl-1-(2,4-dihydroxy-3-trifluoromethyl-phenyl)-ethanone | MS (m/z): 273 (M − 1) |
| 62 | Cyclopentyl-(2,4-dihydroxy-3-trifluoromethyl-phenyl)-methanone | MS (m/z): 273 (M − 1) |
| 63 | 1-(2,4-Bis-benzyloxy-3-trifluoromethyl-phenyl)-3,3-dimethyl-butan-1-one | $^1$H NMR (DMSO-$d_6$) δ 14.37 (s, 1H), 11.70 (s, 1H), 8.10 (d, J = 8.0 Hz, 1H), 6.54 (d, J = 8.0 Hz, 1H), 2.82 (s, 2H), 0.99 (s, 9H) |
| 64 | 2-Cyclopentyl-1-(2,4-dihydroxy-3-trifluoromethyl-phenyl)-ethanone | MS (m/z): 287 (M − 1) |

Preparation 65

Cyclopropyl-(2,4-dihydroxy-3-trifluoromethyl-phenyl)-methanone

Dissolve (2,4-bis-benzyloxy-3-trifluoromethyl-phenyl)-cyclopropyl-methanone (881 mg, 1.86 mmol) in anhydrous tetrahydrofuran (15 mL) and add palladium on carbon (594 mg, 557 μmole). Degas (3×) and hydrogenate at 138 kPa (guage) under hydrogen atmosphere for 4 hrs. Filter the reaction mixture through filter cel and concentrate to provide the crude title compound (470 mg, 1.91 mmol). MS (m/z): 245 (M−1).

Preparation 66

1-(3-Bromo-2,4-dihydroxy-phenyl)-ethanone

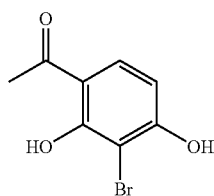

Stir 1-(3-bromo-2-hydroxy-4-methoxy-phenyl)-ethanone (20 g, 82 mmol) in dichloromethane (500 mL) at −30° C. under a nitrogen atmosphere. Treat with boron tribromide (30 mL, 318 mmol) and stir over night at room temperature. Pour mixture into cracked ice and stir for 1 hr. Extract twice with dichloromethane, wash organic layers with water, saturated aqueous sodium chloride solution, dry with magnesium sulfate, filter, and evaporate filtrate. Chromatograph residue on silica gel eluting with 2:1 dichloromethane/hexane to provide the title compound (13.8 g, 74% yield) as an off white powder. $^1$H NMR (CDCl$_3$) δ 13.5 (s, 1H), 7.65 (d, J=8.0 Hz, 1H), 6.62 (d, J=8.0 Hz, 1H), 6.20 (s, 1H), 2.60 (s, 3H).

The following compounds are prepared essentially by the method in Preparation 66.

| Prep. No. | Chemical name | Physical data |
|---|---|---|
| 67 | 1-(3-bromo-2,4-dihydroxyphenyl)-3-methylbutan-1-one | — |
| 68 | 1-(3-bromo-2,4-dihydroxyphenyl)-2-methylpropan-1-one | MS (m/z): 258 (M − 1) |
| 69 | 1-(3-bromo-2,4-dihydroxyphenyl)butan-1-one | MS (m/z): 258 (M − 1) |

Preparation 70

(4-Hydroxymethyl-benzyl)-carbamic acid tert-butyl ester

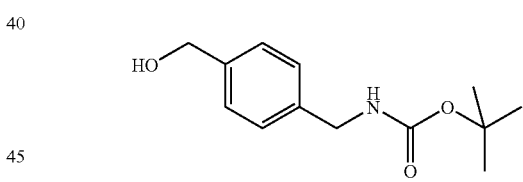

Stir a 1.0M solution of lithium aluminum hydride in tetrahydrofuran (8 L) in a 4-neck 22-L round bottom flask, heat to 40° C., and treat with 4-cyanobenzoic acid (350 g, 2.36 mol), neat, in 25 g portions, at such a rate as to keep the temperature below 60° C. Stir the mixture overnight at room temperature, cool to ~5° C. with an ice bath, treat with water (304 mL), 15% aqueous sodium hydroxide solution (304 mL), and water (912 mL) at such a rate as to keep the temperature below 25° C. during all additions. Remove the ice bath and stir for ~1 hr, then filter, washing the cake with tetrahydrofuran (2 L). Dry the filtrate with magnesium sulfate, filter, and treat the filtrate with di-tert-butyl dicarbonate (576 g, 2.59 mol). Stir overnight at room temperature, then dilute with ethyl ether (7.5 L), wash with brine (2×2 L), dry with magnesium sulfate, filter, and evaporate the filtrate to an off-white solid. Slurry the solid in ethyl acetate (1 L) and hexanes (8 L) and filter to afford the title compound (457 g, 82% yield) as an off-white solid. $^1$H NMR (CDCl$_3$) δ 7.30

(ABq, J=12.0, 8.0 Hz, 4H), 4.8 (bs, 1H), 4.68 (bs, 2H), 4.31 (d, J=4 Hz, 2H), 1.7 (bs, 1H), 1.46 (s, 9H).

Preparation 71

2-Chloro-4-methyl-benzoic acid methyl ester

Add 4N hydrogen chloride in 1,4-dioxane (20 mL, 80 mmol) to 2-chloro-4-methylbenzoic acid (5.0 g, 29.3 mmol) in methanol (60 mL). Stir the reaction mixture at room temperature over the weekend. Concentrate the reaction mixture and partition the residue between ethyl acetate and saturated aqueous sodium bicarbonate solution. Separate the organic layer and extract the aqueous with ethyl acetate (2×). Combine the organic layers, wash with brine, dry over sodium sulfate, and concentrate to provide the title compound as a brownish oil (4.7 g, 25.5 mmol).

The following compounds are prepared essentially by the method of Preparation 71.

| Prep. No. | Chemical name | Physical data |
|---|---|---|
| 72 | 2,3-Difluoro-4-methyl-benzoic acid methyl ester | — |
| 73 | 2-Methoxy-4-methyl-benzoic acid methyl ester | — |

Preparation 74

4-Bromomethyl-2-chloro-benzoic acid methyl ester

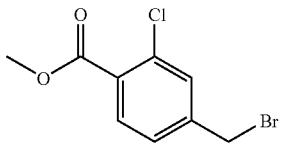

Add benzoyl peroxide (308 mg, 1.27 mmol) to a mixture of methyl-3-chloro-4-metylbenzoate (4.7 g, 25.5 mmol) and N-bromosuccinimide (4.98 g, 28.00 mmol) in anhydrous carbon tetrachloride (100 mL). Reflux the reaction mixture for 4 hrs and cool to room temperature. Filter the reaction mixture and concentrate the filtrate to provide the title compound as a crude oil (7.6 g, 28.8 mmol). MS (m/z): 264 (M+1).

The following compounds are prepared essentially by the method of Preparation 74.

| Prep. No. | Chemical name | Physical data |
|---|---|---|
| 75 | 4-Bromomethyl-2,3-difluoro-benzoic acid methyl ester | — |
| 76 | 4-Bromomethyl-3-chloro-benzoic acid methyl ester | — |
| 77 | 4-Bromomethyl-2-methoxy-benzoic acid methyl ester | MS (m/z): 260 (M + 1) |

Preparation 78

4-Azidomethyl-2-chloro-benzoic acid methyl ester

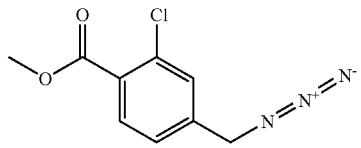

Add sodium azide (2.44 g, 37.49 mmol) to crude 4-bromomethyl-2-chloro-benzoic acid methyl ester (7.6 g, 28.84 mmol) in anhydrous dimethylformamide (100 mL) at room temperature under argon gas. Stir the reaction mixture at 50° C. overnight. Quench the reaction mixture with water and extract with ether (3×). Combine the organic layers, wash with brine, dry over sodium sulfate, and concentrate to provide the crude product (5.8 g, 25.7 mmol).

The following compounds are prepared essentially by the method of Preparation 78.

| Prep. No. | Chemical name | Physical data |
|---|---|---|
| 79 | 4-Azidomethyl-2,3-difluoro-benzoic acid methyl ester | — |
| 80 | 4-Azidomethyl-3-chloro-benzoic acid methyl ester | — |
| 81 | 4-Azidomethyl-3-methoxy-benzoic acid methyl ester | — |
| 82 | 4-Azidomethyl-2-methoxy-benzoic acid methyl ester | MS (m/z): 222 (M + 1) |

Preparation 83

4-Aminomethyl-2-chloro-benzoic acid methyl ester

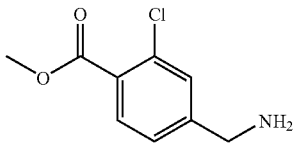

Add triphenylphosphine (30.3 g, 115 mmol) to crude 4-azidomethyl-2-chloro-benzoic acid methyl ester (5.8 g, 25.7 mmol) in tetrahydrofuran (152 mL) and water (4.6 mL). Stir the reaction mixture at room temperature overnight. Concentrate the reaction mixture and partition the residue between 1N hydrochloric acid and ethyl acetate. Separate the organic layer and wash the organic layer with water. Combine the aqueous layers, wash with ethyl acetate, and then neutralize with 1N sodium hydroxide. Extract the resulting aqueous mixture with ethyl acetate (3×). Combine the organic layers, wash with brine, dry over sodium sulfate, and concentrate to provide the crude title compound (2.2 g, 11.0 mmol). MS (m/z): 200 (M+1).

The following compounds are prepared essentially by the method of Preparation 83.

| Prep. No. | Chemical name | Physical data |
|---|---|---|
| 84 | 4-Aminomethyl-2,3-difluoro-benzoic acid methyl ester | MS (m/z): 202 (M + 1) |
| 85 | 4-Aminomethyl-3-chloro-benzoic acid methyl ester | MS (m/z): 200 (M + 1) |

Preparation 86

4-Aminomethyl-3-methoxy-benzoic acid methyl ester

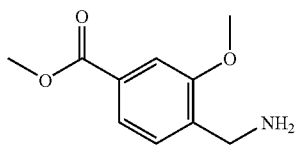

Hydrogenate a mixture of 4-azidomethyl-3-methoxy-benzoic acid methyl ester (4.1 g, 18.5 mmol) and palladium on carbon (4.9 g, 4.63 mmol) in ethanol (200 mL) under a hydrogen atmosphere at 345 KPa for 24 hrs at room temperature. Filter the reaction mixture through diatomaceous earth and concentrate the filtrate to provide the crude title compound (2.9 g, 14.9 mmol). MS (m/z): 196 (M+1). Use it as is in next step.

The following compound is prepared essentially by the method of Preparation 86.

| Prep. No. | Chemical name | Physical data |
|---|---|---|
| 87 | 4-Aminomethyl-2-methoxy-benzoic acid methyl ester | |

Preparation 88

(4-Aminomethyl-3-fluoro-phenyl)-methanol

Add 1M lithium aluminum hydride in tetrahydrofuran (121 mL, 121 mmol) to anhydrous tetrahydrofuran (100 mL) under argon gas. Warm the reaction mixture to 40° C. and add in small portions 4-cyano-3-fluorobenzoic acid (5.0 g, 30.28 mmol) over a 1 hr period. Stir the reaction mixture at 40° C. for 4 hrs and then at room temperature overnight. Cool the reaction mixture to 0° C. and quench by the sequential addition of water (5 mL), 15% sodium hydroxide solution (17 mL), and water (5 mL). Allow the mixture to warm-up to room temperature and stir for 1 hr. Filter the precipitate through diatomaceous earth and concentrate the filtrate to provide the title compound (4.4 g, 28.4 mmol).

Preparation 89

4-Aminomethyl-3-methyl-benzoic acid methyl ester

Add the palladium acetate (1.5 g, 6.5 mmol), 1,1'-bis(diphenylphosphino)ferrocene (4.4 g, 7.9 mmol), 4-bromo-2-methyl-benzonitrile (12.5 g, 64 mmol), methanol (159 ml), acetonitrile (240 ml), triethylamine (46 ml) to the Parr® autoclave. Seal the autoclave, purge with $N_2$ (6×), purge with carbon monoxide (6×), and pressurize with carbon monoxide (862 KPa). Heat the reaction at 100° C. for 24 hrs. Allow the reaction mixture to cool to room temperature and filter. Concentrate the filtrate. Re-dissolve the residue (41 g) in methanol (1 L). Add 7N ammonia in methanol (428 mL) and Raney nickel (8 ml). Purge with nitrogen gas (3×), purge with hydrogen gas (3×), and pressurize with hydrogen gas to 419 KPa. Heat it at 40° C. for 18 hrs. Allow to cool to room temperature and filter the reaction mixture. Concentrate the filtrate to provide the crude title compound (16.8 g).

Preparation 90

4-Cyano-2-fluoro-benzoic acid methyl ester

Add 4N hydrochloride in 1,4-dioxane (100 mL, 400 mmol) to 4-cyano-2-fluoro-benzoic acid (10.0 g, 60.5 mmol) in methanol (100 mL). Stir the reaction mixture at room temperature overnight. Concentrate the reaction mixture. Purify the residue by column chromatography (silica gel) eluting with 20% ethyl acetate/hexane to give the title compound (6.8 g, 38.0 mmol).

Preparation 91

4-Aminomethyl-2-fluoro-benzoic acid methyl ester

Add a slurry of Raney nickel in ethanol (1.2 g, 1.2 ml) to 4-cyano-2-fluoro-benzoic acid methyl ester (5.8 g, 30.0 mmol) in 2N ammonia in methanol (580 mL). Purge with nitrogen gas (3×), purge with hydrogen gas (3×), and pressurize with hydrogen gas to 419 KPa. Heat the reaction at 40° C. for 18 hrs. Allow to cool to room temperature and filter the reaction mixture. Concentrate the filtrate to the crude title compound (6.9 g, 99%). MS (m/z): 184 (M+1).

Preparation 92

4-(tert-Butoxycarbonylamino-methyl)-2-chloro-benzoic acid methyl ester

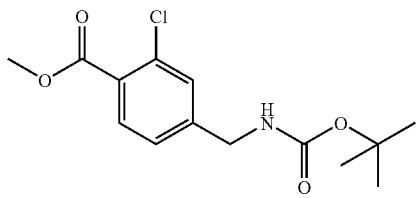

Add di-tert-butyl-dicarbonate (2.65 g, 12.1 mmol) to 4-aminomethyl-2-chloro-benzoic acid methyl ester (2.2 g, 11.0 mmol) in tert-butanol (100 mL). Stir the reaction mixture at 50° C. for 4 hrs. Concentrate the reaction mixture and partition between water and ethyl acetate. Separate the organic layer and extract the aqueous with ethyl acetate (2×). Combine the organic layers, wash with brine, dry over sodium sulfate, and concentrate to provide the title compound (3.2 g, 10.7 mmol). MS (m/z): 322 (M+23).

The following compounds are prepared essentially by the method of Preparation 92.

| Prep. No. | Chemical name | Physical data |
|---|---|---|
| 93 | 4-(tert-Butoxycarbonylamino-methyl)-2,3-difluoro-benzoic acid methyl ester | MS (m/z): 324 (M + 23) |
| 94 | 4-(tert-Butoxycarbonylamino-methyl)-3-chloro-benzoic acid methyl ester | MS (m/z): 322 (M + 23) |
| 95 | 4-(tert-Butoxycarbonylamino-methyl)-3-methoxy-benzoic acid methyl ester | MS (m/z): 318 (M + 23) |
| 96 | 4-(tert-Butoxycarbonylamino-methyl)-2-methoxy-benzoic acid methyl ester | MS (m/z): 296 (M + 1) |
| 97 | (2-Fluoro-4-hydroxymethyl-benzyl)-carbamic acid tert-butyl ester | MS (m/z): 278 (M + 23) |
| 98 | 4-(tert-Butoxycarbonylamino-methyl)-2-fluoro-benzoic acid methyl ester | MS (m/z): 306 (M + 23) |
| 99 | 4-(tert-Butoxycarbonylamino-methyl)-3-methyl-benzoic acid methyl ester | MS (m/z): 302 (M + 23) |

Preparation 100

4-[(tert-Butoxycarbonyl-methyl-amino)-methyl]-3-methyl-benzoic acid methyl ester Add in portions of 60% sodium hydride dispersion in oil (472 mg, 11.81 mmol) to 4-(tert-butoxycarbonylamino-methyl)-3-methyl-benzoic acid methyl ester (3.0 g, 10.74 mmol) in anhydrous dimethylformamide (50 mL) at 0° C. under argon gas. After complete addition, stir the reaction mixture for 15 min at 0° C. Add methyl iodide (735 μL, 11.8 mmol) to the reaction mixture. Allow the reaction mixture to warm-up to room temperature and stir overnight. Quench the reaction mixture with saturated aqueous ammonium chloride and extract with ethyl acetate (3×). Combine the organic layers, wash with brine, dry over sodium sulfate, and concentrate. Purify the residue by chromatography (silica gel) eluting with 25% ethyl acetate/hexane to give the title compound. MS (m/z): 316 (M+23).

Preparation 101

(3-Chloro-4-hydroxymethyl-benzyl)-carbamic acid tert-butyl ester

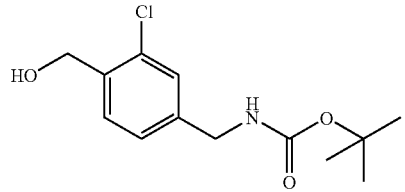

Add 1M lithium aluminum hydride in tetrahydrofuran (32 mL, 32 mmol) to anhydrous tetrahydrofuran (240 mL) at room temperature under argon gas, cool to 0° C. and add slowly a solution of 4-(tert-butoxycarbonylamino-methyl)-2-chloro-benzoic acid methyl ester (3.2 g, 10.7 mmol) in tetrahydrofuran (120 mL). The reaction mixture is stirred at 0° C. for 45 min. Quench the reaction mixture with saturated aqueous ammonium chloride and extract with ethyl acetate (3×). Combine the organic layers, wash with brine, dry over sodium sulfate, and concentrate. Purify the residue by chromatography (silica gel) eluting with 35% ethyl acetate/hexane to give the title compound (2.1 g, 7.7 mmol). MS (m/z): 294 (M+23).

The following compounds are prepared essentially by the method of Preparation 101.

| Prep. No. | Chemical name | Physical data |
|---|---|---|
| 102 | (2,3-Difluoro-4-hydroxymethyl-benzyl)-carbamic acid tert-butyl ester | MS (m/z): 296 (M + 23) |
| 103 | (2-Chloro-4-hydroxymethyl-benzyl)-carbamic acid tert-butyl ester | MS (m/z): 294 (M + 23) |
| 104 | (4-Hydroxymethyl-2-methoxy-benzyl)-carbamic acid tert-butyl ester | MS (m/z): 290 (M + 23) |
| 105 | (4-Hydroxymethyl-3-methoxy-benzyl)-carbamic acid tert-butyl ester | MS (m/z): 290 (M + 23) |

-continued

| Prep. No. | Chemical name | Physical data |
|---|---|---|
| 106 | (4-Hydroxymethyl-2-methyl-benzyl)-carbamic acid tert-butyl ester | MS (m/z): 274 (M + 23) |
| 107 | (4-Hydroxymethyl-2-methyl-benzyl)-methyl-carbamic acid tert-butyl ester | MS (m/z): 288 (M + 23) |
| 108 | (3-Fluoro-4-hydroxymethyl-benzyl)-carbamic acid tert-butyl ester | MS (m/z): 278 (M + 23) |

Preparation 109

(3-Iodomethyl-benzyl)-carbamic acid tert-butyl ester

Stir polystyrene-bound triphenylphosphine (4.27 g, 12.8 mmol) and imidazole (0.86 g, 12.7 mmol) in dichloromethane (45 mL). Add a solution of (3-hydroxymethyl-benzyl)-carbamic acid tert-butyl ester (1.70 g, 6.1 mmol) in dichloromethane (45 mL). Add iodine (3.22 g, 12.7 mmol) in 3 portions. Stir 16 hrs. Filter through a pad of diatomaceous earth. Wash with aqueous sodium thiosulfate. Dry the organic portion over sodium sulfate. Filter and concentrate. Chromatograph the residue on silica eluting with 25% ethyl acetate/dichloromethane to provide the title compound (2.53 g, 7.3 mmol).

Preparation 110

3-(tert-Butoxycarbonylamino-methyl)-benzoic acid methyl ester

Stir 3-aminomethyl-benzoic acid methyl ester hydrochloride (2.13 g, 10.6 mmol) in a mixture of dichloromethane (200 mL) and saturated aqueous sodium bicarbonate (100 mL). Add di-tert-butyl-dicarbonate (2.76 g, 12.7 mmol) and stir for 2 hrs. Separate the organic phase and dry over sodium sulfate. Filter and concentrate. Purify the residue by chromatography (silica get) eluting with 20-30% ethyl acetate/hexane to provide the title compound (2.8 g, 100%).

Preparation 111

3-[(tert-Butoxycarbonyl-methyl-amino)-methyl]-benzoic acid methyl ester

Dissolve 3-(tert-butoxycarbonylamino-methyl)-benzoic acid methyl ester (2.80 g, 10.6 mmol) in dimethylformamide (60 mL). Add 60% sodium hydride dispersion in oil (0.52 g, 13 mmol). Stir for 1 hr. Add methyl iodide (0.81 mL, 13 mmol) and stir for additional 1 hr. Quench the reaction with water and concentrate. Partition the residue between ethyl acetate and water. Separate the organic layer and dry over sodium sulfate. Filter and concentrate. Purify the residue by chromatography (silica gel) eluting with 15-25% ethyl acetate/hexane to provide the title compound (1.70 g, 57%).

Preparation 112

(3-Hydroxymethyl-benzyl)-methyl-carbamic acid tert-butyl ester

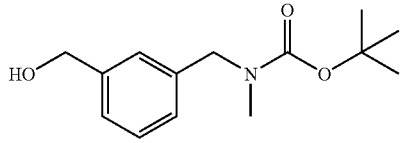

Dissolve 3-[(tert-butoxycarbonyl-methyl-amino)-methyl]-benzoic acid methyl ester (1.70 g, 6.1 mmol) in tetrahydrofuran (60 mL) at 0° C. Add a 1M solution of lithium aluminum hydride in tetrahydrofuran (8 mL, 8 mmol) dropwise and stir for 2 hrs. Quench the reaction with water (3 mL), 5N sodium hydroxide solution (3 mL) and more water (9 mL), filter and concentrate. Purify the residue by chromatography (silica gel) eluting with 40-60% ethyl acetate/hexanes to provide the title compound (1.42 g, 93%).

Preparation 113

6-Hydroxymethyl-nicotinic acid methyl ester

Add 2,5-pyridinedicarboxylic acid dimethyl ester (15 g, 76.8 mmol), calcium chloride (34.12 g, 307.4 mmol), ethanol (100 mL) and tetrahydrofuran (100 mL) into a reaction flask. Cool the mixture to 0° C. Add sodium borohydride (3.49 g, 92.3 mmol) slowly to the reaction mixture. Maintain the temperature of the reaction mixture at 0° C. and stir the mixture for 7 hrs. Remove the solid by filtration. Pour the mixture onto ice. Extract with dichloromethane (100 mL×4). Combine organic layers and dry with sodium sulfate. Remove solvent under reduced pressure to give 9.6 g (75% yield) of the crude product of 6-hydroxymethyl-nicotinic acid methyl ester. MS (m/z): 168.3 (M+1).

Preparation 114

6-Chloromethyl-nicotinic acid methyl ester

Add 6-hydroxymethyl-nicotinic acid methyl ester (9.6 g, 57.4 mmol) and dichloromethane (200 mL) to a flask and cool to 0° C. Add thionyl chloride (10.25 g, 86.14 mmol). Stir the mixture at room temperature for 1 hr. Concentrate the reaction mixture under reduce pressure to give the crude 6-chloromethyl-nicotinic acid methyl ester (13 g, 102% yield) as a yellow solid. MS (m/z): 223 (M+1).

Preparation 115

6-Azidomethyl-nicotinic acid methyl ester

Add 6-chloromethyl-nicotinic acid methyl ester (9.1 g, 40.98 mmol) and dimethylsulfoxide (100 mL) into a flask and cool to 0° C. Add sodium azide (4 g, 61.47 mmol) and sodium carbonate (13 g, 122.9 mmol) to the reaction mixture. Let the mixture slowly warm to room temperature. Stir for 1 hr at room temperature. Add water (100 mL) to the mixture. Extract with diethyl ether (100 mL×3). Wash the organic layer with water and brine. Dry with sodium sulfate. Remove solvent under reduced pressure to give the product (6.8 g, 86% yield) as light yellow oil. MS (m/z): 193.3 (M+1).

Preparation 116

6-Aminomethyl-pyridin-3-yl-methanol

Add 6-azidomethyl-nicotinic acid methyl ester (2.3 g, 11.97 mmol) and tetrahydrofuran (100 mL) in a flask and cool to 0° C. Add 1M lithium aluminum hydride solution in tetrahydrofuran (17.95 mL, 17.95 mmol) slowly. Stir the mixture for 30 min. Quench the reaction with ice. Add 10 mL of saturated Rochelle's salt solution. Stir for 30 min. Filter, remove the solvent under reduced pressure to give 6-aminomethyl-pyridin-3-yl-methanol (1.6 g, 97% yield) as a yellow oil.

Preparation 117

5-Hydroxymethyl-pyridin-2-ylmethyl)-carbamic acid tert-butyl ester

Add 6-aminomethyl-pyridin-3-yl-methanol (1.6 g, 11.58 mmol) and tetrahydrofuran (50 mL) to a flask. Then add di-tert-butyl-dicarbonate (3.79 g, 17.3 mmol) to the reaction mixture. Stir for 30 min. Concentrate to give residue. Purify the product by chromatography (silica gel) eluting with methanol in dichloromethane (95:5 to 9:1) to afford of 5-hydroxymethyl-pyridin-2-ylmethyl)-carbamic acid tert-butyl ester (2.03 g, 73%). MS (m/z): 239.3 (M+1).

Preparation 118

(3-Chloro-4-methyl-benzyl)-carbamic acid tert-butyl ester

Add di-tert-butyl-dicarbonate (15.3 g, 70.0 mmol) to 3-chloro-4-methylbenzylamine (9.9 g, 63.6 mmol) in tert-butyl alcohol (250 mL) at room temperature. Stir at room temperature for 2 hrs and heat at 50° C. for 3 hrs. Concentrate the reaction mixture and partition between water and ethyl acetate. Separate the organic layer and extract the aqueous with ethyl acetate (2×). Combine the organic layers, wash with brine, dry over sodium sulfate, and concentrate to provide the title compound (16.2 g, 63.3 mmol). MS (m/z): 278 (M+23).

Preparation 119

(3-Chloro-4-methyl-benzyl)-dicarbamic acid di-tert-butyl ester

Add di-tert-butyl-dicarbonate (7.51 g, 34.4 mmoles), diisopropylethylamine (6.0 mL, 34.41 mmol) and dimethylaminopyridine (382 mg, 3.13 mmol) to (3-chloro-4-methyl-benzyl)-carbamic acid tert-butyl ester (8.0 g, 31.3 mmol) in anhydrous dichloromethane (150 mL) at room temperature. Stir the reaction at room temperature overnight. Concentrate the reaction mixture and partition the residue between ethyl acetate and water. Separate the organic layer and extract the aqueous with ethyl acetate (2×). Combine the organic layers, wash with brine, dry over sodium sulfate, and concentrate. Purify the residue by chromatography (silica gel) eluting with 15% ethyl acetate/hexane to give the title compound (3.3 g, 9.27 mmol). MS (m/z): 378 (M+23).

Preparation 120

(4-Bromomethyl-3-chloro-benzyl)-dicarbamic acid di-tert-butyl ester

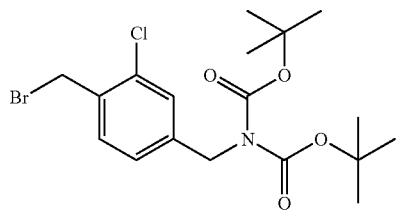

Add benzoyl peroxide (34 mg, 140 mmol) to a mixture of (3-chloro-4-methyl-benzyl)-dicarbamic acid di-tert-butyl ester (1.0 g, 2.8 mmol) and N-bromosuccinimide (550 mg, 3.1 mmol) in anhydrous carbon tetrachloride (22 mL) at room temperature under argon gas. Reflux the reaction mixture for 4 hrs and cool to room temperature overnight. Filter the reaction mixture and concentrate the filtrate. Purify the residue by chromatography (silica gel) eluting with 20% ethyl acetate/hexane to give the title compound (614 mg). MS (m/z): 457 (M+23).

Preparation 121

1-Trityl-1H-imidazole-4-carboxylic acid methyl ester

Add triethylamine (1.88 mL, 13.48 mmol) to a mixture of methyl-4-imidazolecarboxylate (1.0 g, 7.93 mmol) and triphenylmethyl chloride (2.43 g, 8.72 mmol) in anhydrous acetonitrile (25 mL) over 10 min at room temperature and stir overnight. Quench with water and extract with ethyl acetate (3×). Combine the organic layers, wash with 1N hydrochloride solution, water, saturated aqueous sodium bicarbonate solution and brine sequentially, dry over sodium sulfate, and concentrate to provide the title compound 1-trityl-1H-imidazole-4-carboxylic acid methyl ester (2.8 g, 7.60 mmol).

Preparation 122

1-Trityl-1H-imidazole-4-carboxylic acid

Add 1N sodium hydroxide (22.8 mL, 22.8 mmol) to 1-trityl-1H-imidazole-4-carboxylic acid methyl ester (2.8 g, 7.60 mmol) in tetrahydrofuran (20 mL) and methanol (20 mL) at room temperature. Stir the reaction mixture at room temperature for 5 hrs. Acidify the reaction mixture with 5N aqueous hydrochloride to pH about 6. Filter and dry the solid to give the title compound as a white solid (2 g, 5.64 mmol).

Preparation 123

1-Isopropyl-1H-imidazole-4-carboxylic acid methyl ester

Add sodium hydride (2.87 g, 71.7 mmol, 60% in mineral oil) portion-wise over 10 minutes to a cooled (0° C.) solution of 1H-imidazole-4-carboxylic acid methyl ester (6.03 g, 47.8 mmol) in dimethylformamide (150 ml). Remove the cooling bath and stir at room temperature for 4.5 hrs. Cool the mixture to 0° C. and add isopropyl iodide (8.94 g, 52.6 mmol) dropwise over 10 min. Remove the cooling bath and stir at room temperature for 20 hrs. Quench the mixture with saturated aqueous ammonium chloride and extract with ethyl acetate (3×). Wash the combined extracts with brine, dry over sodium sulfate, filter and concentrate under reduced pressure to give an oil. Purify the oil by flash chromatography (silica gel) eluting with 25% acetone/hexanes to provide the product as an oil (1.41 g, 8.4 mmol, 17% yield). M/S (m/z): 169 (M+H).

Preparation 124

1-Isopropyl-1H-imidazole-4-carboxylic acid

Add a solution of lithium hydroxide monohydrate (1.06 g, 25.1 mmol) in water (8 ml) to a solution of 1-isopropyl-1H-imidazole-4-carboxylic acid methyl ester (1.41 g, 8.38 mmol) in methanol (10 ml) and tetrahydrofuran (8 ml). Stir at room temperature for 20 hrs. Concentrate to give a solid. Dissolve the solid in a small amount of water and adjust to pH 4 with 5N hydrochloric acid. Wash the aqueous layer with ethyl acetate, and then concentrate the aqueous layer to provide the crude product as a solid (2.09 g). MS (m/z): 155 (M+H).

Preparation 125

{4-[3-Hydroxy-4-(3-methyl-butyryl)-2-trifluoromethyl-phenoxymethyl]-benzyl}-carbamic acid tert-butyl ester

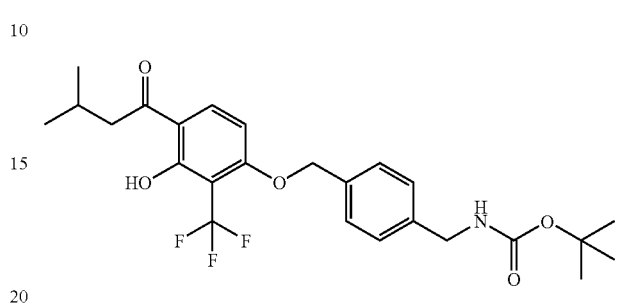

Mix 1-(2,4-dihydroxy-3-trifluoromethyl-phenyl)-3-methyl-butan-1-one (2 g, 7.63 mmol), (4-hydroxymethyl-benzyl)-carbamic acid tert-butyl ester (1.99 g, 8.39 mmol) and triphenylphosphine (2.20 g, 8.39 mmol) in anhydrous toluene (125 mL) at room temperature under argon gas. Slowly add diisopropyl azodicarboxylate (1.70 g, 8.39 mmol, 1.7 mL) over 30 min. Stir the reaction mixture at room temperature overnight. Concentrate the mixture under reduced pressure and purify the residue by flash chromatography (silica gel) eluting with using 25% ethyl acetate/hexane to provide the product as a white solid (1.5 g, 3.12 mmol, 41% yield). MS (m/z): 480 (M−1).

The following compounds are prepared essentially by the method of Preparation 125.

| Prep. No. | Chemical name | Physical data |
|---|---|---|
| 126 | {4-[4-(2-Cyclopentyl-acetyl)-3-hydroxy-2-trifluoromethyl-phenoxymethyl]-benzyl}-carbamic acid tert-butyl ester | MS (m/z): 506 (M − 1) |
| 127 | {4-[4-(3,3-Dimethyl-butyryl)-3-hydroxy-2-trifluoromethyl-phenoxymethyl]-benzyl}-carbamic acid tert-butyl ester | MS (m/z): 494 (M − 1) |
| 128 | {4-[4-(2-Cyclopropyl-acetyl)-3-hydroxy-2-trifluoromethyl-phenoxymethyl]-benzyl}-carbamic acid tert-butyl ester | MS (m/z): 478 (M − 1) |
| 129 | [4-(4-Cyclopropanecarbonyl-3-hydroxy-2-trifluoromethyl-phenoxymethyl)-benzyl]-carbamic acid tert-butyl ester | MS (m/z): 464 (M − 1) |
| 130 | {3-Chloro-4-[4-(3,3-dimethyl-butyryl)-3-hydroxy-2-trifluoromethyl-phenoxymethyl]-benzyl}-carbamic acid tert-butyl ester | MS (m/z): 528 (M − 1) |
| 131 | [2,3-Difluoro-4-(3-hydroxy-4-isobutyryl-2-trifluoromethyl-phenoxymethyl)-benzyl]-carbamic acid tert-butyl ester | MS (m/z): 502 (M − 1) |
| 132 | [2-Chloro-4-(3-hydroxy-4-isobutyryl-2-trifluoromethyl-phenoxymethyl)-benzyl]-carbamic acid tert-butyl ester | MS (m/z): 500 (M − 1) |
| 133 | [4-(3-Hydroxy-4-isobutyryl-2-trifluoromethyl-phenoxymethyl)-2-methoxy-benzyl]-carbamic acid tert-butyl ester | MS (m/z): 496 (M − 1) |
| 134 | {4-[4-(3,3-Dimethyl-butyryl)-3-hydroxy-2-trifluoromethyl-phenoxymethyl]-3-methoxy-benzyl}-carbamic acid tert-butyl ester | MS (m/z): 524 (M − 1) |
| 135 | [2-Fluoro-4-(3-hydroxy-4-isobutyryl-2-trifluoromethyl-phenoxymethyl)-benzyl]-carbamic acid tert-butyl ester | MS (m/z): 484 (M − 1) |
| 136 | [4-(3-Hydroxy-4-isobutyryl-2-trifluoromethyl-phenoxymethyl)-2-methyl-benzyl]-carbamic acid tert-butyl ester | MS (m/z): 480 (M − 1) |
| 137 | {4-[4-(3,3-Dimethyl-butyryl)-3-hydroxy-2-trifluoromethyl-phenoxymethyl]-2-methyl-benzyl}-carbamic acid tert-butyl ester | MS (m/z): 508 (M − 1) |

-continued

| Prep. No. | Chemical name | Physical data |
|---|---|---|
| 138 | [4-(3-Hydroxy-4-isobutyryl-2-trifluoromethyl-phenoxymethyl)-2-methyl-benzyl]-methyl-carbamic acid tert-butyl ester | MS (m/z): 494 (M − 1) |
| 139 | [3-Fluoro-4-(3-hydroxy-4-isobutyryl-2-trifluoromethyl-phenoxymethyl)-benzyl]-carbamic acid tert-butyl ester | MS (m/z): 484 (M − 1) |
| 140 | tert-butyl 4-((4-acetyl-2-bromo-3-hydroxyphenoxy)methyl)benzylcarbamate | MS (m/z): 449 (M − 1) |
| 141 | tert-butyl 4-((2-bromo-3-hydroxy-4-(3-methylbutanoyl)phenoxy)methyl)benzylcarbamate | MS (m/z): 491 (M − 1) |
| 142 | [4-(4-Cyclopentanecarbonyl-3-hydroxy-2-trifluoromethyl-phenoxymethyl)-benzyl]-carbamic acid tert-butyl ester | MS (m/z): 492 (M − 1) |
| 143 | [4-(4-Butyryl-3-hydroxy-2-trifluoromethyl-phenoxymethyl)-benzyl]-carbamic acid tert-butyl ester | MS (m/z): 466 (M − 1) |
| 144 | [4-(3-Hydroxy-2-methyl-4-propionyl-phenoxymethyl)-benzyl]-carbamic acid tert-butyl ester | MS (m/z): 398 (M − 1) |
| 145 | [4-(3-Hydroxy-4-isobutyryl-2-trifluoromethyl-phenoxymethyl)-benzyl]-carbamic acid tert-butyl ester | MS (m/z): 466 (M − 1) |
| 146 | [4-(4-Cyclobutanecarbonyl-3-hydroxy-2-trifluoromethyl-phenoxymethyl)-benzyl]-carbamic acid tert-butyl ester | MS (m/z): 502 (M + 1) |
| 147 | {4-[4-(2-Cyclobutyl-acetyl)-3-hydroxy-2-trifluoromethyl-phenoxymethyl]-benzyl}-carbamic acid tert-butyl ester | MS (m/z): 516 (M + 1) |
| 148 | tert-Butyl 3-((4-acetyl-3-hydroxy-2-(trifluoromethyl)phenoxy)methyl)benzyl(methyl)carbamate | MS (m/z): 452 (M − 1) |
| 149 | 5-(4-Acetyl-3-hydroxy-2-trifluoromethyl-phenoxymethyl)-pyridin-2-ylmethyl]-carbamic acid tert-butyl ester | — |

Preparation 150

[3-Chloro-4-(3-hydroxy-4-isobutyryl-2-trifluoromethyl-phenoxymethyl)-benzyl]-dicarbamic acid di-tert-butyl ester

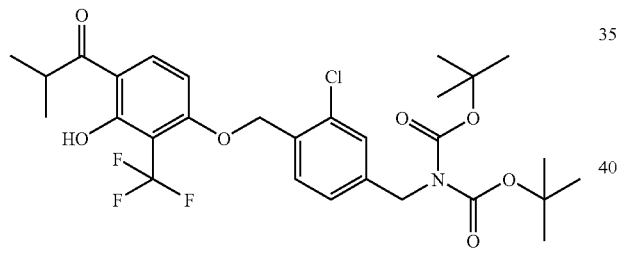

Add crude (4-bromomethyl-3-chloro-benzyl)-dicarbamic acid di-tert-butyl ester (614 mg) to a solution of 1-(2,4-dihydroxy-3-trifluoromethyl-phenyl)-2-methyl-propan-1-one (385 mg, 1.55 mmol) in anhydrous dimethylformamide (25 mL). Add lithium carbonate (219 mg, 2.97 mmol) to the reaction mixture and heat at 60° C. for 20 hrs. Cool to room temperature and filter the reaction mixture. Quench the filtrate into water and extract with ethyl acetate (3×). Combine the organic layers, wash with brine, dry over sodium sulfate, and concentrate. Purify the residue by flash column chromatography (silica gel) eluting with 20% ethyl acetate/hexane to give the title compound (320 mg) which still contains an impurity. MS (m/z): 500 (M–$C_4H_9OCO$).

The following compound is prepared essentially by the method of Preparation 150.

| Prep. No. | Chemical name | Physical data |
|---|---|---|
| 151 | [3-(4-Acetyl-3-hydroxy-2-trifluoromethyl-phenoxymethyl)-benzyl]-carbamic acid tert-butyl ester | MS (m/z): 438.0 (M − 1). |

Preparation 152

1-[4-(4-Aminomethyl-benzyloxy)-2-hydroxy-3-trifluoromethyl-phenyl]-2-methyl-propan-1-one hydrochloride

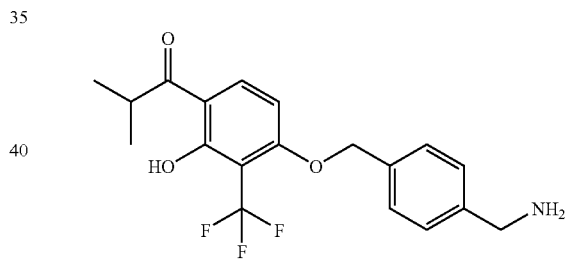

Mechanically stir solutions of 1-(2,4-dihydroxy-3-trifluoromethyl-phenyl)-2-methyl-propan-1-one (211 g, 850.1 mmol), (4-hydroxymethyl-benzyl)-carbamic acid tert-butyl ester (195 g, 821.8 mmol), and triphenylphosphine (212 g; 808.3 mmol) in toluene (9 L) in two separate 22-L Morton flasks. Treat solutions with diisopropyl azodicarboxylate (183 mL, 923 mmol) over a 60 min period, then stir over the weekend at room temperature. Combine the solutions and evaporate to a brown oil. Dissolve the oil in 1,4-dioxane (8 L), treat with 4N hydrogen chloride solution in 1,4-dioxane (3 L, 12 mole), and heat to 92° C. for 6 hrs (out-gassing and precipitation is observed at 52° C. during the warm up period). Cool to room temperature, filter the resulting solid and wash with dioxane, 30% dioxane in hexanes, and hexanes to provide the title compound (510 g, 78% yield) as a tan solid. HPLC $R_t$=4.71 min; $^1$H NMR (DMSO-$d_6$) δ 14.00 (s, 1H), 8.4 (bs, 3H), 7.50 (ABq, J=12.0, 8.0 Hz, 4H), 6.92 (d, J=8.0 Hz, 1H), 5.37 (s, 2H), 4.0 (m, 2H), 3.73 (hept, J=4.0 Hz, 1H), 1.12 (d, J=4.0 Hz, 6H); $^{19}$F NMR (DMSO-$d_6$) δ-54.10; MS (m/z): 368.0 (M+1).

Preparation 153

1-[4-(4-Aminomethyl-benzyloxy)-2-hydroxy-3-trifluoromethyl-phenyl]-3-methyl-butan-1-one hydrochloride

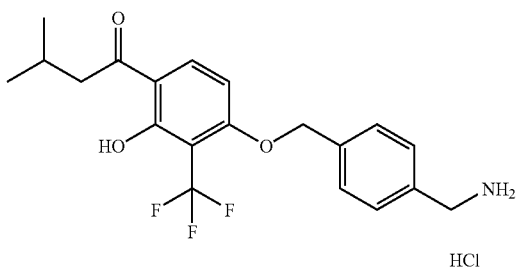

Add 4M hydrogen chloride in 1,4-dioxane (25 mL) to a mixture of {4-[3-hydroxy-4-(3-methyl-butyryl)-2-trifluoromethyl-phenoxymethyl]-benzyl}-carbamic acid tert-butyl ester (1.4 g, 2.91 mmol) in anhydrous 1,4-dioxane (25 mL) and heat the reaction at 50° C. for 1.5 hrs. Cool the reaction mixture to room temperature, dilute with ethyl acetate, and filter to provide the product as a white solid (934 mg, 2.24 mmol, 77% yield).

The following compounds are prepared essentially by the method of Preparation 153.

| Prep. No. | Chemical name | Physical data |
| --- | --- | --- |
| 154 | 1-[4-(4-Aminomethyl-benzyloxy)-2-hydroxy-3-trifluoromethyl-phenyl]-2-cyclopentyl-ethanone hydrochloride | MS (m/z): 408 (M + 1, free base) |
| 155 | 1-[4-(4-Aminomethyl-benzyloxy)-2-hydroxy-3-trifluoromethyl-phenyl]-3,3-dimethyl-butan-1-one hydrochloride | MS (m/z): 396 (M + 1, free base) |
| 156 | 1-[4-(4-Aminomethyl-benzyloxy)-2-hydroxy-3-trifluoromethyl-phenyl]-2-cyclopropyl-ethanone hydrochloride | MS (m/z): 380 (M + 1, free base) |
| 157 | [4-(4-Aminomethyl-benzyloxy)-2-hydroxy-3-trifluoromethyl-phenyl]-cyclopropyl-methanone hydrochloride | MS (m/z): 366 (M + 1, free base) |
| 158 | 1-[4-(4-Aminomethyl-2-chloro-benzyloxy)-2-hydroxy-3-trifluoromethyl-phenyl]-3,3-dimethyl-butan-1-one hydrochloride | MS (m/z): 429 (M + 1, free base) |
| 159 | 1-[4-(4-Aminomethyl-2,3-difluoro-benzyloxy)-2-hydroxy-3-trifluoromethyl-phenyl]-2-methyl-propan-1-one hydrochloride | MS (m/z): 403 (M + 1, free base) |
| 160 | 1-[4-(4-Aminomethyl-3-chloro-benzyloxy)-2-hydroxy-3-trifluoromethyl-phenyl]-2-methyl-propan-1-one hydrochloride | MS (m/z): 401 (M + 1, free base) |
| 161 | 1-[4-(4-Aminomethyl-3-methoxy-benzyloxy)-2-hydroxy-3-trifluoromethyl-phenyl]-2-methyl-propan-1-one hydrochloride | MS (m/z): 398 (M + 1, free base) |
| 162 | 1-[4-(4-Aminomethyl-2-methoxy-benzyloxy)-2-hydroxy-3-trifluoromethyl-phenyl]-3,3-dimethyl-butan-1-one hydrochloride | MS (m/z): 426 (M + 1, free base) |
| 163 | 1-[4-(4-Aminomethyl-3-fluoro-benzyloxy)-2-hydroxy-3-trifluoromethyl-phenyl]-2-methyl-propan-1-one hydrochloride | MS (m/z): 385 (M + 1, free base) |
| 164 | 1-[4-(4-Aminomethyl-3-methyl-benzyloxy)-2-hydroxy-3-trifluoromethyl-phenyl]-2-methyl-propan-1-one hydrochloride | MS (m/z): 382 (M + 1, free base) |
| 165 | 1-[4-(4-Aminomethyl-3-methyl-benzyloxy)-2-hydroxy-3-trifluoromethyl-phenyl]-3,3-dimethyl-butan-1-one hydrochloride | MS (m/z): 410 (M + 1, free base) |
| 166 | 1-[2-Hydroxy-4-(3-methyl-4-methylaminomethyl-benzyloxy)-3-trifluoromethyl-phenyl]-2-methyl-propan-1-one hydrochloride | MS (m/z): 396 (M + 1, free base) |
| 167 | 1-[4-(4-Aminomethyl-2-fluoro-benzyloxy)-2-hydroxy-3-trifluoromethyl-phenyl]-2-methyl-propan-1-one hydrochloride | MS (m/z): 386 (M + 1, free base) |
| 168 | 1-(4-(4-(aminomethyl)benzyloxy)-3-bromo-2-hydroxyphenyl)ethanone hydrochloride | MS (m/z): 387 (M + 1, free base) |
| 169 | 1-(4-(4-(aminomethyl)benzyloxy)-3-bromo-2-hydroxyphenyl)-3-methylbutan-1-one hydrochloride | MS (m/z): 393 (M + 1, free base) |

-continued

| Prep. No. | Chemical name | Physical data |
|---|---|---|
| 170 | [4-(4-Aminomethyl-benzyloxy)-2-hydroxy-3-trifluoromethyl-phenyl]-cyclopentyl-methanone hydrochloride | MS (m/z): 394 (M + 1, free base) |
| 171 | 1-[4-(4-Aminomethyl-benzyloxy)-2-hydroxy-3-trifluoromethyl-phenyl]-butan-1-one hydrochloride | MS (m/z): 368 (M + 1, free base) |
| 172 | 1-[4-(4-Aminomethyl-benzyloxy)-2-hydroxy-3-methyl-phenyl]-propan-1-one hydrochloride | MS (m/z): 330 (M + 1, free base) |
| 173 | 1-[4-(4-Aminomethyl-benzyloxy)-2-hydroxy-3-trifluoromethyl-phenyl]-2-methyl-propan-1-one hydrochloride | MS (m/z): 368 (M + 1, free base) |
| 174 | [4-(4-Aminomethyl-benzyloxy)-2-hydroxy-3-trifluoromethyl-phenyl]-cyclobutyl-methanone hydrochloride | MS (m/z): 380 (M + 1, free base) |
| 175 | 1-[4-(4-Aminomethyl-benzyloxy)-2-hydroxy-3-trifluoromethyl-phenyl]-2-cyclobutyl-ethanone hydrochloride | MS (m/z): 394 (M + 1, free base) |
| 176 | 1-[4-(6-Aminomethyl-pyridin-3-ylmethoxy)-2-hydroxy-3-trifluoromethyl-phenyl]-ethanone hydrochloride | MS (m/z): 477.0 (M + 1, free base) |
| 177 | 1-[2-Hydroxy-4-(3-methylaminomethyl-benzyloxy)-3-trifluoromethyl-phenyl]-ethanone hydrochloride | MS (m/z) 354.2 (M + 1, free base); 352.2 (M − 1, free base) |
| 178 | 1-[4-(3-Aminomethyl-benzyloxy)-2-hydroxy-3-trifluoromethyl-phenyl]-ethanone hydrochloride | MS (m/z) 340.0 (M + 1, free base); 338.0 (M − 1, free base) |
| 179 | 1-[4-(4-Aminomethyl-2-chloro-benzyloxy)-2-hydroxy-3-trifluoromethyl-phenyl]-2-methyl-propan-1-one hydrochloride | MS (m/z): 402 (M + 1, free base) |

Preparation 180

1-Trityl-1H-imidazole-4-carboxylic acid 4-[4-(3,3-dimethyl-butyryl)-3-hydroxy-2-trifluoromethyl-phenoxymethyl]-benzylamide Add 1-hydroxybenzotriazole hydrate (63.8 mg; 417 µmol), 1-trityl-1H-imidazole-4-carboxylic acid (148 mg, 417 µmol) and 1-(3-dimethylaminopropyl)-3-ethylcarbodiimide hydrochloride (79.9 mg, 417 µmol) to anhydrous acetonitrile (7 mL). Stir the reaction mixture at room temperature for 1 hr. Then add 1-[4-(4-aminomethyl-benzyloxy)-2-hydroxy-3-trifluoromethyl-phenyl]-3,3-dimethyl-butan-1-one hydrochloride (150 mg, 347 µmol) and triethylamine (97 µL, 695 µmol). Stir the reaction mixture at room temperature overnight. Quench the reaction with water and the solid, filter the solid and dry to give the title compound (220 mg, 301 µmol). MS (m/z): 730 (M−1).

Preparation 181

4-(aminomethyl)phenylmethanol hydrochloride

Add 4N hydrogen chloride in 1,4-dioxane (25 mL) to a solution of (4-hydroxymethyl-benzyl)-carbamic acid tert-butyl ester (3.0 g, 12.6 mmol) in 1,4-dioxane (25 mL). Heat the reaction mixture at 50° C. for 1 hr. Filter the solid and wash it with ethyl acetate to give the title compound (2.1 g, 12.1 mmol).

Preparation 182

N-(4-(Hydroxymethyl)benzyl)-1-methyl-1H-imidazole-4-carboxamide

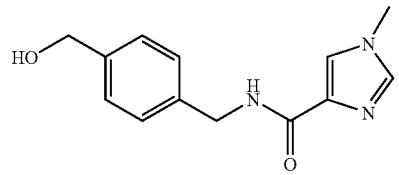

Stir a mixture of 1-methyl-1H-imidazole-4-carboxylic acid (4.0 g, 31.67 mmol), 1-(3-dimethylaminopropyl)-3-ethylcarbodiimide hydrochloride (6.6 g, 34.5 mmol) and 1-hydroxybenzotriazole hydrate (5.29 g, 34.5 mmoles) in anhydrous acetonitrile (150 mL) at room temperature for 1 hr. Add to the reaction mixture (4-aminomethyl-phenyl)-methanol hydrochloride (5.0 g, 28.8 mmol) and triethylamine (8.4 mL, 60.5 mmol). Stir the reaction mixture at room temperature overnight. Quench the reaction mixture with water and extract with ethyl acetate (3×). Combine the organic layers, wash with brine, dry over sodium sulfate, and concentrate to provide the title compound (4.6 g, 18.8 mmol). MS (m/z): 246 (M+1).

Preparation 183

N-(4-(Iodomethyl)benzyl)-1-methyl-1H-imidazole-4-carboxamide

Gently stir for 30 min a mixture of polymer supported triphenylphosphine (1.0 g, 3 mmol/g, 3.0 mmol), 1H-imidazole (208 mg, 3.06 mmol), and iodine (776 mg; 3.06 mmol) in anhydrous dichloromethane (12 mL). To the reaction mixture, add a mixture of N-(4-(hydroxymethyl)benzyl)-1-methyl-1H-imidazole-4-carboxamide (500 mg, 2.04 mmol) in anhydrous dichloromethane (5.0 mL). Gently stir the reaction mixture for 5 hrs at room temperature. Filter the reaction mixture and wash the filtrate with an aqueous 10% sodium thiosulfate solution. Separate the aqueous layer. Wash the organic layer with water, dry over magnesium sulfate, and concentrate to the title compound (532 mg, 1.50 mmol). MS (m/z): 356 (M+1).

EXAMPLE 1

1-Methyl-1H-imidazole-4-carboxylic acid 4-(3-hydroxy-4-isobutyryl-2-trifluoromethyl-phenoxymethyl)-benzylamide

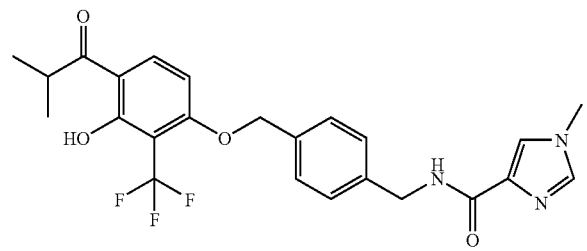

Mechanically stir suspensions of 1-[4-(4-aminomethyl-benzyloxy)-2-hydroxy-3-trifluoromethyl-phenyl]-2-methyl-propan-1-one hydrochloride (244 g, 604 mmol), 1-methyl-imidazole-4-carboxylic acid (95 g, 753 mmol), and 1-hydroxybenzotriazole hydrate (118 g, 770 mmol) in tetrahydrofuran (8 L) in two separate 22-L Morton flasks. Treat each solution with diisopropylethylamine (269 mL, 1.54 mol) and 1-(3-dimethylaminopropyl)-3-ethylcarbodiimide hydrochloride (145 g, 756 mmol) in single portions and stir overnight at room temperature. Dilute each with 4 L of water and extract twice with 4 L of ethyl acetate. Wash organic layers with saturated sodium chloride solution, dry with magnesium sulfate, filter, and evaporate the filtrates to tan foams. Combine the foams and recrystallize from isopropanol (6 L) to afford the title compound (426 g, 74% yield). m.p. 164.7° C.; HPLC $R_t$=4.86 min; $^1$H NMR (DMSO-$d_6$) δ 13.95 (s, 1H), 8.45 (t, J=8.0 Hz, 1H), 8.27 (d, J=8.0 Hz, 1H), 7.63 (d, J=12.0 Hz, 2H), 7.33 (ABq, J=12.0, 8.0 Hz, 4H), 6.89 (d, J=8.0 Hz, 1H), 5.32 (s, 2H), 4.39 (d, J=8.0 Hz, 2H), 3.71 (hept, J=8.0 Hz, 1H), 3.67 (s, 3H), 1.12 (d, J=8.0 Hz, 6H); $^{19}$F NMR (DMSO-$d_6$) δ-54.10; MS (m/z): 476.0 (M+1).

EXAMPLE 2

1-Methyl-1H-imidazole-4-carboxylic acid 4-[3-hydroxy-4-(3-methyl-butyryl)-2-trifluoromethyl-phenoxymethyl]-benzylamide

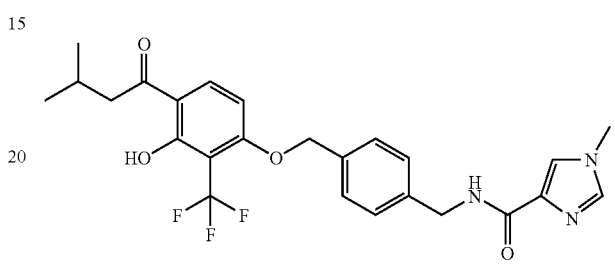

Mix 1-[4-(4-aminomethyl-benzyloxy)-2-hydroxy-3-trifluoromethyl-phenyl]-3-methyl-butan-1-one hydrochloride (120 mg, 287.2 µmol), 1-methyl-1-H-imidazole-4-carboxylic acid (43.5 mg, 344.6 µmol), 1-hydroxybenzotriazole hydrate (52.8 mg, 344.6 µmol) in anhydrous tetrahydrofuran (4.5 mL). Add triethylamine (72.7 mg, 718 µmol, 100 µL) and 1-(3-dimethylaminopropyl)-3-ethylcarbodiimide hydrochloride (66.1 mg, 344.6 µmol) to the mixture. Stir the reaction mixture at room temperature overnight. Dilute the reaction mixture with water. Extract the mixture with ethyl acetate (3×). Combine the organic layers, wash with brine, dry over sodium sulfate, and concentrate under reduced pressure. Purify the crude residue by flash chromatography (silica gel) eluting with 5% methanol/ethyl acetate followed by reverse phase chromatography using 90/10 to 20/80 (water/0.1% trifluoroacetic acid)/acetonitrile to provide the product as a white solid (75 mg, 153 µmol, 53.4% yield). MS (m/z): 490 (M+1).

The following compounds are prepared essentially by the method of Example 2.

| Exp. No. | Chemical name | Physical data |
| --- | --- | --- |
| 3 | 1-Methyl-1H-imidazole-4-carboxylic acid 4-[4-(2-cyclopentyl-acetyl)-3-hydroxy-2-trifluoromethyl-phenoxymethyl]-benzylamide | MS (m/z): 516 (M + 1) |
| 4 | 1-Methyl-1H-imidazole-4-carboxylic acid 4-[4-(3,3-dimethyl-butyryl)-3-hydroxy-2-trifluoromethyl-phenoxymethyl]-benzylamide | MS (m/z): 504 (M + 1) |
| 5 | 1H-Imidazole-4-carboxylic acid 4-[3-hydroxy-4-(3-methyl-butyryl)-2-trifluoromethyl-phenoxymethyl]-benzylamide | MS (m/z): 476 (M + 1) |
| 6 | 1-Methyl-1H-imidazole-2-carboxylic acid 4-[4-(3,3-dimethyl-butyryl)-3-hydroxy-2-trifluoromethyl-phenoxymethyl]-benzylamide | MS (m/z): 504 (M + 1) |
| 7 | 1-Methyl-1H-imidazole-4-carboxylic acid 4-[4-(2-cyclopropyl-acetyl)-3-hydroxy-2-trifluoromethyl-phenoxymethyl]-benzylamide | MS (m/z): 488 (M + 1) |
| 8 | 1-Methyl-1H-imidazole-4-carboxylic acid 4-(3-hydroxy-4-isobutyryl-2-trifluoromethyl-phenoxymethyl)-benzylamide | MS (m/z): 476.0 (M + 1) |
| 9 | 3-Ethyl-3H-imidazole-4-carboxylic acid 4-(3-hydroxy-4-isobutyryl-2-trifluoromethyl-phenoxymethyl)-benzylamide | MS (m/z): 490 (M + 1) |

| Exp. No. | Chemical name | Physical data |
|---|---|---|
| 10 | 1-Methyl-1H-imidazole-4-carboxylic acid 4-(4-cyclopropanecarbonyl-3-hydroxy-2-trifluoromethyl-phenoxymethyl)-benzylamide | MS (m/z): 474 (M + 1) |
| 11 | 1-Methyl-1H-imidazole-4-carboxylic acid 3-chloro-4-[4-(3,3-dimethyl-butyryl)-3-hydroxy-2-trifluoromethyl-phenoxymethyl]-benzylamide | MS (m/z): 538 (M + 1) |
| 12 | 1-Methyl-1H-imidazole-4-carboxylic acid 2,3-difluoro-4-(3-hydroxy-4-isobutyryl-2-trifluoromethyl-phenoxymethyl)-benzylamide | MS (m/z): 512 (M + 1) |
| 13 | 1-Methyl-1H-imidazole-4-carboxylic acid 2-chloro-4-(3-hydroxy-4-isobutyryl-2-trifluoromethyl-phenoxymethyl)-benzylamide | MS (m/z): 510 (M + 1) |
| 14 | 1-Methyl-1H-imidazole-4-carboxylic acid 4-(3-hydroxy-4-isobutyryl-2-trifluoromethyl-phenoxymethyl)-2-methoxy-benzylamide | MS (m/z): 506 (M + 1) |
| 15 | 1-Methyl-1H-imidazole-4-carboxylic acid 4-[4-(3,3-dimethyl-butyryl)-3-hydroxy-2-trifluoromethyl-phenoxymethyl]-3-methoxy-benzylamide | MS (m/z): 534 (M + 1) |
| 16 | 1-Methyl-1H-imidazole-4-carboxylic acid 2-fluoro-4-(3-hydroxy-4-isobutyryl-2-trifluoromethyl-phenoxymethyl)-benzylamide | MS (m/z): 494 (M + 1) |
| 17 | 1-Methyl-1H-imidazole-4-carboxylic acid 4-(3-hydroxy-4-isobutyryl-2-trifluoromethyl-phenoxymethyl)-2-methyl-benzylamide | MS (m/z): 490 (M + 1) |
| 18 | 1-Methyl-1H-imidazole-4-carboxylic acid 4-[4-(3,3-dimethyl-butyryl)-3-hydroxy-2-trifluoromethyl-phenoxymethyl]-2-methyl-benzylamide | MS (m/z): 518 (M + 1) |
| 19 | 1-Methyl-1H-imidazole-4-carboxylic acid [4-(3-hydroxy-4-isobutyryl-2-trifluoromethyl-phenoxymethyl)-2-methyl-benzyl]-methyl-amide | MS (m/z): 504 (M + 1) |
| 20 | 1-Methyl-1H-imidazole-4-carboxylic acid 3-fluoro-4-(3-hydroxy-4-isobutyryl-2-trifluoromethyl-phenoxymethyl)-benzylamide | MS (m/z): 494 (M + 1) |
| 21 | 1-Methyl-1H-imidazole-4-carboxylic acid 3-chloro-4-(3-hydroxy-4-isobutyryl-2-trifluoromethyl-phenoxymethyl)-benzylamide | MS (m/z): 510 (M + 1) |
| 22 | N-(4-((4-acetyl-2-bromo-3-hydroxyphenoxy)methyl)benzyl)-1-methyl-1H-imidazole-4-carboxamide | MS (m/z): 459 (M + 1) |
| 23 | N-(4-((2-bromo-3-hydroxy-4-(3-methylbutanoyl)phenoxy)methyl)benzyl)-1-methyl-1H-imidazole-4-carboxamide | MS (m/z): 501 (M + 1) |
| 24 | 1-Methyl-1H-imidazole-4-carboxylic acid 4-(4-butyryl-3-hydroxy-2-trifluoromethyl-phenoxymethyl)-benzylamide | MS (m/z): 476 (M + 1) |
| 25 | 1-Methyl-1H-imidazole-4-carboxylic acid 4-(3-hydroxy-4-propionyl-2-trifluoromethyl-phenoxymethyl)-benzylamide | MS (m/z): 462 (M + 1) |
| 26 | 1-Methyl-1H-imidazole-4-carboxylic acid 4-(3-hydroxy-2-methyl-4-propionyl-phenoxymethyl)-benzylamide | MS (m/z): 408 (M + 1) |
| 27 | 3-Methyl-3H-imidazole-4-carboxylic acid 4-(4-acetyl-3-hydroxy-2-trifluoromethyl-phenoxymethyl)-benzylamide | MS (m/z): 448 (M + 1) |
| 28 | 1-Isopropyl-1H-imidazole-4-carboxylic acid 4-(3-hydroxy-4-isobutyryl-2-trifluoromethyl-phenoxymethyl)-benzylamide | MS (m/z): 502 (M − 1) |
| 29 | 1-Methyl-1H-imidazole-4-carboxylic acid 4-(4-acetyl-3-hydroxy-2-trifluoromethyl-phenoxymethyl)-benzylamide | MS (m/z): 448 (M + 1) |
| 30 | N-(4-((4-(cyclobutanecarbonyl)-3-hydroxy-2-(trifluoromethyl)phenoxy)methyl)benzyl)-1-methyl-1H-imidazole-4-carboxamide | MS (m/z): 488 (M + 1) |
| 31 | N-(4-((4-(2-cyclobutylacetyl)-3-hydroxy-2-(trifluoromethyl)phenoxy)methyl)benzyl)-1-methyl-1H-imidazole-4-carboxamide | MS (m/z): 502 (M + 1) |
| 32 | 1-Methyl-1H-imidazole-4-carboxylic acid [5-(4-acetyl-3-hydroxy-2-trifluoromethyl-phenoxymethyl)-pyridin-2-ylmethyl]-amide | MS (m/z): 449.3 (M + 1) |
| 33 | 3-Methyl-3H-imidazole-4-carboxylic acid 3-(4-acetyl-3-hydroxy-2-trifluoromethyl-phenoxymethyl)-benzylamide | MS (m/z) 448 (M + 1); 446 (M − 1) |
| 34 | N-(4-((4-(cyclopentanecarbonyl)-3-hydroxy-2-(trifluoromethyl)phenoxy)methyl)benzyl)-1-methyl-1H-imidazole-4-carboxamide | MS (m/z): 502 (M + 1) |

EXAMPLE 35

1-Methyl-1H-imidazole-4-carboxylic acid 3-chloro-4-[4-(3,3-dimethyl-butyryl)-3-hydroxy-2-trifluoromethyl-phenoxymethyl]-benzylamide hydrochloride

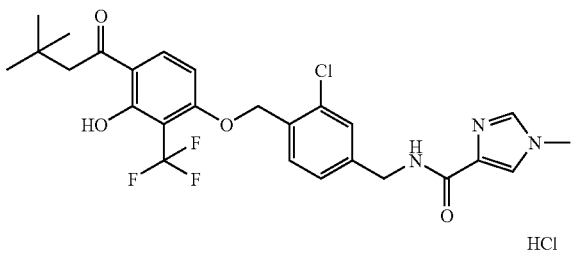

HCl

Add acetone (2 mL) to 1-methyl-1H-imidazole-4-carboxylic acid 3-chloro-4-[4-(3,3-dimethyl-butyryl)-3-hydroxy-2-trifluoromethyl-phenoxymethyl]-benzylamide (140 mg, 260.24 μmol) in ethyl acetate (5 mL) to make a solution. Add 4N hydrogen chloride in dioxane (2 mL, 8.00 mmol) to the solution. A precipitate forms upon addition. Concentrate the mixture and triturate the resulting solid with ethyl acetate. Filter the solid to give the title compound (115 mg). MS (m/z): 538 (M+1, free base).

The following compounds are prepared essentially by the method of Example 35.

EXAMPLE 45

1H-Imidazole-4-carboxylic acid 4-[4-(3,3-dimethyl-butyryl)-3-hydroxy-2-trifluoromethyl-phenoxymethyl]-benzylamide

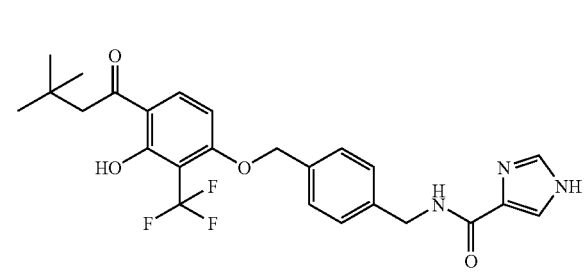

Add a 2.5N solution of hydrogen chloride (10 mL, 25.00 mmol) to 1-trityl-1H-imidazole-4-carboxylic acid 4-[4-(3,3-dimethyl-butyryl)-3-hydroxy-2-trifluoromethyl-phenoxymethyl]-benzylamide (217 mg, 296 μmol) in ethanol (10 mL). Stir the reaction mixture for 1.5 hr at 60° C. Cool the reaction mixture to room temperature and filter the precipitate. To the filtrate add water to precipitate the product. Filter the precipitate and triturate it with ether to remove the remaining trityl impurity. Filter the solid to give the title compound as a white solid (121 mg, 83% yield). MS (m/z): 490 (M+1).

| Exp. No. | Chemical name | Physical data |
|---|---|---|
| 36 | 1-Methyl-1H-imidazole-4-carboxylic acid 2-chloro-4-(3-hydroxy-4-isobutyryl-2-trifluoromethyl-phenoxymethyl)-benzylamide hydrochloride | MS (m/z): 510 (M + 1, free base) |
| 37 | 1-Methyl-1H-imidazole-4-carboxylic acid 2-fluoro-4-(3-hydroxy-4-isobutyryl-2-trifluoromethyl-phenoxymethyl)-benzylamide hydrochloride | MS (m/z): 494 (M + 1, free base) |
| 38 | 1-Methyl-1H-imidazole-4-carboxylic acid [4-(3-hydroxy-4-isobutyryl-2-trifluoromethyl-phenoxymethyl)-2-methyl-benzyl]-methyl-amide hydrochloride | MS (m/z): 504 (M + 1, free base) |
| 39 | 1-Methyl-1H-imidazole-4-carboxylic acid 4-[(2-cyclopentyl-acetyl)-3-hydroxy-2-trifluoromethyl-phenoxymethyl]-benzylamide hydrochloride | M/S (m/z): 516 (M + 1, free base) |
| 40 | 1-Methyl-1H-imidazole-4-carboxylic acid [5-(4-acetyl-3-hydroxy-2-trifluoromethyl-phenoxymethyl)-pyridin-2-ylmethyl]-amide hydrochloride | MS (m/z): 449.0 (M + 1, free base) |
| 41 | 3-Methyl-3H-imidazole-4-carboxylic acid [3-(4-acetyl-3-hydroxy-2-trifluoromethyl-phenoxymethyl)-benzyl]-methyl-amide hydrochloride | MS (m/z) 462.2 (M + 1, free base) |
| 42 | 1-Methyl-1H-imidazole-4-carboxylic acid 4-(4-cyclopentanecarbonyl-3-hydroxy-2-trifluoromethyl-phenoxymethyl)-benzylamide hydrochloride | MS (m/z): 502 (M + 1, free base) |
| 43 | 1-Methyl-1H-imidazole-4-carboxylic acid 4-(4-acetyl-3-hydroxy-2-trifluoromethyl-phenoxymethyl)-benzylamide hydrochloride | MS (m/z): 448 (M + 1, free base) |
| 44 | 1-Methyl-1H-imidazole-4-carboxylic acid 4-(3-hydroxy-4-isobutyryl-2-trifluoromethyl-phenoxymethyl)-benzylamide hydrochloride | MS (m/z): 476 (M + 1, free base) |

EXAMPLE 46

3-Methyl-3H-imidazole-4-carboxylic acid [3-(4-acetyl-3-hydroxy-2-trifluoromethyl-phenoxymethyl)-benzyl]-methyl-amide hydrochloride

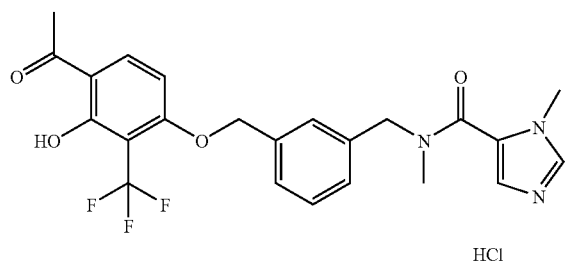

HCl

Stir 1-[2-hydroxy-4-(3-methylaminomethyl-benzyloxy)-3-trifluoromethyl-phenyl]-ethanone hydrochloride (200 mg, 0.51 mmol), 3-methyl-3H-imidazole-4-carboxylic acid (96 mg, 0.76 mmol), 1-(3-dimethylaminopropyl)-3-ethylcarbodiimide hydrochloride (173 mg, 0.9 mmol), 1-hydroxybenzotriazole monohydrate (123 mg, 0.9 mmol) and triethylamine (350 uL, 2.5 mmol) in tetrahydrofuran (15 mL). After 16 hrs, dilute the reaction mixture with ethyl acetate and wash with aqueous sodium carbonate solution. Dry the organic portion over sodium sulfate. Filter and concentrate. Chromatograph the crude material on silica gel eluting with 4% methanol/dichloromethane to provide the coupling product: the 3-methyl-3H-imidazole-4-carboxylic acid [3-(4-acetyl-3-hydroxy-2-trifluoromethyl-phenoxymethyl)-benzyl]-methyl-amide. Dissolve it in methanol, add 5N hydrogen chloride. Concentrate to a minimal volume. Add ethyl acetate to precipitate a white solid. Collect the solid, wash it with ethyl acetate and vacuum-dry to provide the title compound (186 mg). MS (m/z): 462.2 (M+1, free base).

EXAMPLE 47

N-(4-((2-bromo-3-hydroxy-4-isobutyrylphenoxy)methyl)benzyl)-1-methyl-1H-imidazole-4-carboxamide

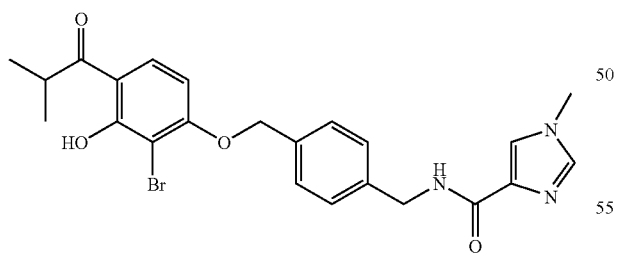

Add lithium carbonate (24 mg, 324 μmol) to 1-(3-bromo-2,4-dihydroxy-phenyl)-2-methyl-propan-1-one (70 mg, 270 μmol) and N-(4-(iodomethyl)benzyl)-1-methyl-1H-imidazole-4-carboxamide (106 mg, 297 μmol) in anhydrous dimethylformamide (4 mL). Warm the reaction mixture to 50° C. and stir for 1.5 hrs. Add additional N-(4-(iodomethyl)benzyl)-1-methyl-1H-imidazole-4-carboxamide (20 mg, 56 μmol) and stir for 1 hr at 50° C. Add additional lithium carbonate (24 mg, 324 μmol) and N-(4-(iodomethyl)benzyl)-1-methyl-1H-imidazole-4-carboxamide (20 mg, 56 μmol) and stir overnight at 50° C. Cool the reaction mixture to room temperature and quench with water. Extract the aqueous mixture with ethyl acetate (3×). Combine the organic layers, wash with brine, dry over sodium sulfate, and concentrate. Purify the residue by reverse phase HPLC using gradient 90/10 to 20/80 (water/0.1% trifluoroacetic acid)/acetonitrile as eluent to give the title compound (22 mg, 45 μmol). MS (m/z): 487 (M+1).

The following compound is prepared essentially by the method of Example 47.

| Exp. No. | Chemical name | Physical data |
| --- | --- | --- |
| 48 | N-(4-((2-bromo-4-butyryl-3-hydroxyphenoxy)methyl)benzyl)-1-methyl-1H-imidazole-4-carboxamide | MS (m/z): 485 (M − 1) |

We claim:
1. A compound of formula I or a pharmaceutically acceptable salt thereof

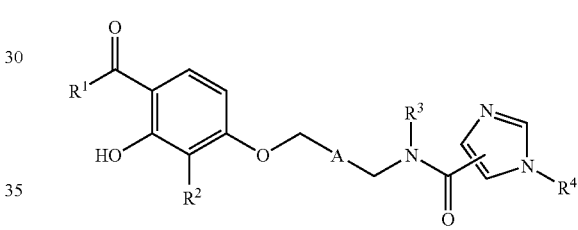

wherein

R$^1$ is C$_1$-C$_5$ alkyl, C$_3$-C$_5$ cycloalkyl, or C$_3$-C$_5$ cycloalkyl-methyl;

R$^2$ is C$_1$-C$_3$ alkyl, chloro, bromo, fluoro or trifluoromethyl;

A is selected from the group consisting of

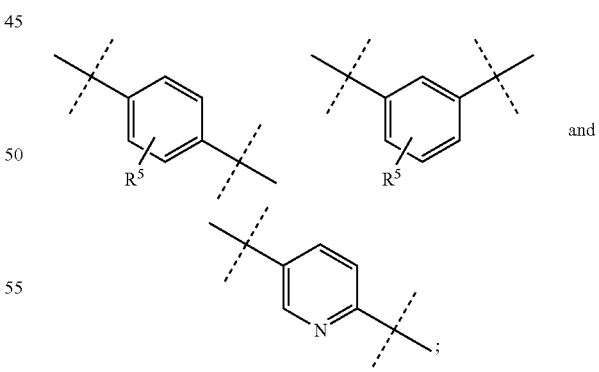

R$^3$ is hydrogen or methyl;

R$^4$ is hydrogen or C$_1$-C$_3$ alkyl; and

R$^5$ is one substituent selected from the group consisting of hydrogen, methyl, methoxy, chloro and fluoro; or two substituents which are fluoro.

2. The compound of claim 1, or a pharmaceutically acceptable salt thereof wherein A is 3. The compound of claim 1 which is a compound of formula Ia, or a pharmaceutically acceptable salt thereof, Ia wherein
- R$^1$ is C$_1$-C$_5$ alkyl, C$_3$-C$_5$ cycloalkyl, or C$_3$-C$_5$ cycloalkylmethyl;
- R$^2$ is C$_1$-C$_3$ alkyl, bromo or trifluoromethyl;
- R$^3$ is hydrogen or methyl;
- R$^4$ is hydrogen or C$_1$-C$_3$ alkyl; and
- R$^5$ is one substituent selected from the group consisting of hydrogen, methyl, methoxy, chloro and fluoro; or two substituents which are fluoro.

4. The compound of claim 1, or a pharmaceutically acceptable salt thereof, wherein R$^1$ is C1-C5 alkyl.

5. The compound of claim 1, or a pharmaceutically acceptable salt thereof, wherein R$^2$ is trifluoromethyl.

6. The compound of claim 1, or a pharmaceutically acceptable salt thereof, wherein R$^3$ is hydrogen.

7. The compound of claim 1, or a pharmaceutically acceptable salt thereof, wherein R$^4$ is C1-C3 alkyl.

8. The compound of claim 1, or a pharmaceutically acceptable salt thereof, wherein R$^5$ is hydrogen, methyl or methoxy.

9. The compound of claim 1, or a pharmaceutically acceptable salt thereof, wherein R$^5$ is hydrogen.

10. The compound of claim 1, or a pharmaceutically acceptable salt thereof, wherein R$^4$ is methyl.

11. The compound of claim 1, or a pharmaceutically acceptable salt thereof, wherein R$^1$ is isopropyl.

12. The compound of claim 1, or a pharmaceutically acceptable salt thereof, wherein
- R$^1$ is methyl, ethyl, propyl, isopropyl, isobutyl, 2,2-dimethylpropyl, cyclopropyl, cyclobutyl, cyclopentyl, cyclopropylmethyl, cyclobutylmethyl or cyclopentylmethyl;
- R$^2$ is methyl, trifluoromethyl or bromo;

A is selected from the group consisting of

R$^3$ is hydrogen or methyl; and
R$^4$ is hydrogen, methyl, ethyl or isopropyl.

13. The compound of claim 1 which is 1-methyl-1H-imidazole-4-carboxylic acid 4-(3-hydroxy-4-isobutyryl-2-trifluoromethyl-phenoxymethyl)-benzylamide or a pharmaceutically acceptable salt thereof.

14. The compound of claim 1 which is 1-methyl-1H-imidazole-4-carboxylic acid 4-(3-hydroxy-4-isobutyryl-2-trifluoromethyl-phenoxymethyl)-benzylamide.

15. A pharmaceutical composition comprising a compound as claimed in claim 1, or a pharmaceutically acceptable salt thereof, and a pharmaceutically acceptable carrier, diluent or excipient.

16. A method of treating depression, comprising administering to a patient in need thereof an effective amount of a compound as claimed in claim 1, or a pharmaceutically acceptable salt thereof.

* * * * *

UNITED STATES PATENT AND TRADEMARK OFFICE
CERTIFICATE OF CORRECTION

PATENT NO. : 7,754,742 B2  Page 1 of 1
APPLICATION NO. : 12/502252
DATED : July 13, 2010
INVENTOR(S) : Albert Khilevich et al.

It is certified that error appears in the above-identified patent and that said Letters Patent is hereby corrected as shown below:

Column 51, line 39 - In Claim 4, delete "C1-C5" and insert -- $C_1$-$C_5$ --, therefor.

Column 51, line 46 - In Claim 7, delete "C1-C3" and insert -- $C_1$-$C_3$ --, therefor.

Signed and Sealed this

Thirty-first Day of August, 2010

David J. Kappos
*Director of the United States Patent and Trademark Office*